(12) United States Patent
Rao et al.

(10) Patent No.: US 7,335,686 B2
(45) Date of Patent: Feb. 26, 2008

(54) METHOD AND COMPOSITION FOR TREATING OSTEOPOROSIS

(75) Inventors: Kanury Venkata Subba Rao, New Delhi (IN); Mohan Ramachandran Wani, Maharashtra (IN); Venkatasamy Manivel, New Delhi (IN); Parameswaran Perunninakulath Subrayan, Goa (IN); Vinod Kumar Singh, Kanpur (IN); Ramasamy Vijaya Anand, Kanpur (IN); Ehrlich Desa, Goa (IN); Gyan Chandra Mishra, Pune (IN); Anil Chatterji, Goa (IN)

(73) Assignee: Council of Scientific and Industrial Research, New Delhi (IN)

( * ) Notice: Subject to any disclaimer, the term of this patent is extended or adjusted under 35 U.S.C. 154(b) by 282 days.

(21) Appl. No.: 10/747,671

(22) Filed: Dec. 30, 2003

(65) Prior Publication Data

US 2005/0085537 A1   Apr. 21, 2005

Related U.S. Application Data

(60) Provisional application No. 60/512,183, filed on Oct. 20, 2003.

(51) Int. Cl.
*A61K 31/195* (2006.01)

(52) U.S. Cl. .................................................. 514/562
(58) Field of Classification Search ................ None
See application file for complete search history.

(56) References Cited

U.S. PATENT DOCUMENTS 6,905,710 B2 * 6/2005 Wani et al. .................. 424/547
6,977,084 B2 * 12/2005 Bui et al. ..................... 424/442

* cited by examiner

*Primary Examiner*—Raymond J. Henley, III
(74) *Attorney, Agent, or Firm*—Womble Carlyle Sandridge Rice

(57) ABSTRACT

This invention relates to a novel class of acidic amino acid/dicarboxylic acid derivatives (sulfonic acid/sulfate derivatives of naturally occurring amino acids and their amides) useful as inhibitors of osteoclastogenesis. The invention also provides methods of using the novel class of acidic amino acid/dicarboxylic acid derivatives of the general formula $ZOC-(CRR)_m-COOH$, wherein: m=2, 3 or 4; Z is OH or $NH_2$; one R in the compound is from the group consisting of $SO_3H$, $OSO_3H$, $CH_2-SO_3H$, $CH_2-OSO_3H$, and $NHSO_3H$, and the remaining Rs are H or $NH_2$, for inhibition of osteoclastogenesis.

14 Claims, 2 Drawing Sheets
(2 of 2 Drawing Sheet(s) Filed in Color)

PLATE 1

A

B

PLATE 2

A

B

METHOD AND COMPOSITION FOR TREATING OSTEOPOROSIS

RELATED APPLICATIONS

This application claims priority to U.S. Provisional Patent Application No. 60/512,183, filed Oct. 20, 2003, whose contents are incorporated by reference.

FIELD OF THE INVENTION

This invention relates to a novel class of acidic amino acid/dicarboxylic acid derivatives (sulfonic acid/sulfate derivatives of naturally occurring amino acids and their amides) useful as inhibitors of osteoclastogenesis. More particularly, this invention relates to inhibitors of osteoclastogenesis containing novel class of acidic amino acid/dicarboxylic acid derivatives of the general formula: ZOC—$(CRR)_m$—COOH, wherein: m=2, 3 or 4; Z is OH or $NH_2$; one R in the compound is from the group consisting of $SO_3H$, $OSO_3H$, $CH_2$—$SO_3H$, $CH_2$—$OSO_3H$, and $NHSO_3H$, and the remaining Rs are H or $NH_2$. Thus, the compounds may bear the general formula ZOC—$CR_7R_8$—$CR_5R_6$—$CR_3R_4$—$CR_1R_2$—COOH, ZOC—$CR_5R_6$—$CR_3R_4$—$CR_1R_2$—COOH or ZOC—$CR_3R_4$—$CR_1R_2$—COOH wherein Z is OH or $NH_2$, and $R_1$ to $R_8$ denotes H, $NH_2$, $SO_3H$, or $OSO_3H$, $CH_2$—$SO_3H$, $CH_2$—$OSO_3H$, $NHSO_3H$.

A pharmaceutical composition containing the aforementioned inhibitors of osteoclastogenesis may also contain different divalent metal ions such as Mg, Ca or Zn. The composition consists of varying amounts of the above acidic amino acid/dicarboxylic acid derivatives and their pharmaceutically acceptable selected alkali/alkaline earth metal salts. The invention also provides a process for the preparation of the aforesaid compounds, useful for the inhibition of the osteoclast differentiation, maturation and activation. These compounds can also be used for developing effective drugs for the treatment of osteoporosis, osteoarthritis, bone metastasis and bone loss in other metabolic diseases of clinical importance.

1) The inhibitors of osteoclastogenesis also contain different divalent metal ions such as Mg, Ca or Zn, wherein all the symbols are the same meaning as hereinafter defined and non-toxic salts thereof as an active ingredient,
2) The composition consists of varying amounts of the above acidic amino acid/dicarboxylic acid derivatives and their pharmaceutically acceptable selected alkali/alkaline earth metal salts, wherein all the symbols are the same meaning as hereinafter defined and non-toxic salts thereof as an active ingredient,
3) The process for the preparation of the aforesaid compounds, useful for the inhibition of the osteoclast differentiation, maturation and activation.
4) These compounds can also be used for developing effective drugs for the treatment of osteoporosis, osteoarthritis, bone metastasis and bone loss in other metabolic diseases of clinical importance.

BACKGROUND OF THE INVENTION

Indian green mussels (*Perna viridis*) are the cheap source of proteins and considered as a delicacy. Extract prepared from green mussels by enzyme-acid hydrolysis process showed various biological activities. In our earlier patent (US patent application #20030044470) we have shown the inhibition of osteoclast differentiation and activation in the crude extract. In same continuation, attempts have been made to purify the active compound that showed inhibition of osteoclast differentiation and activation. The purification of the crude extract was done using HPLC, gel filtration and TLC methods. The purified compound was again checked for the above activity. The compound was characterized using NMR and LC-MS/MS techniques. This compound was synthesized and checked for the presence of the above biological activity. This patent in particular describes the synthesis of the compound and also its activity for inhibition of osteoclast formation.

Novel class of amino acid/dicarboxylic acid derivatives (sulfonic acid/sulfate derivatives of naturally occurring amino acids and their amides) along with calcium is for their activation to show inhibition of the osteoclastogenesis. Amino acid derivatives and calcium ion when used separately did not show any activity on inhibition of the osteoclastogenesis. The following classes of compounds are identified (1) Natural acidic amino acids (Aspartic acid, Glutamic acid and their amides),
(2) Unnatural amino acids, amides such as homoglutamic acid,
(3) Dicarboxylic acids such as succinic acid, glutaric acid, and adipic acid
(4) N-sulfonyl, C-sulfonyl/sulfate derivatives of the above acids
(5) Alkaline earth metals such as Mg, Zn and Ca as their suitable salts.

Related Arts

A lot of information is available on the matrix metalloproteinases (MMP's) commonly used as MMP inhibitors for the treatment of osteoporosis (Nigel, R. A. Beeley, Phillip, R. J., Ansell, Andrew, J. P., Dochert, 1994, Curr. Opin. Ther. Patents., 4, 7-16). A cylinder shaped solid compound has been prepared from the atelocollagen solution, L-alanine solution and bone morphogenetic protein for treating bone loss and elevating bone deformities (Hiroo, Akhihiko, Rebecca, Wozney, Seeherman, 2003, WO Patent #2003066083). In another study glutamate and glutamate derivatives/analogs or their mixtures have been used for modulating the bone quality (Tadeusz, Jose Luis; Stefan, 2003, WO Patent # 2003043626). Toshhiro (2003) invented a compound consisting of interacting trans-activators with glutamic acid, aspartic acid and rich carboxyl-terminal domain for estrogen receptor dependent activity (Toshihiro, 2002, WO Patent # 2003000730). Glutamic acid has been defined as an effective neuromediator and one of its derivatives is involved in osteoclast formation and bone resorption. The modification of glutamic acid action in bone could be used for bone remodeling (Hopital E. Herriot, Lyon Fr., 2002, Microscopy Research and technique, 58(2), 70-76).

However, these inhibitors have various problems and efforts were made for the development of non-peptide inhibitors. For instance in the specification of EP 606046, several aryl-sulfonamide derivatives have been described. In another invention several aryl sulfonyl amino acid derivatives of the following specifications have been described (Sakaki, Kanazawa, Sugiura, Miyazaki, Ohno, 2002, U.S. Pat. No. 6,403,644) as MMP inhibitors:
1) N-[[4-(Benzoylamino)phenyl]sulfonyl]glycine,
2) N-[[3-(Benzoylamino)phenyl]sulfonyl]glycine,
3) N-[[2-(Benzoylamino)phenyl]sulfonyl]glycine,
4) N-[[4-(Acetylamino)phenyl]sulfonyl]glycine,
5) N-[[4-(Phenylacetylamino)phenyl]sulfonyl]glycine, 6) N-[[4-[(Phenylethylcarbonyl)amino]phenyl]sulfonyl]glycine,
7) N-[[4-(Cinnamoylamino)phenyl]sulfonyl]glycine,
8) N-[[4-(N-Phenylureido)phenyl]sulfonyl]glycine,
9) N-[[4-(N-Phenylthioureido)phenyl]sulfonyl]glycine,
10) N-[[4-[(Benzyloxycarbonyl)amino]phenyl]sulfonyl] glycine,
11) N-[[4-[(Phenyloxymethylcarbonyl)amino]phenyl]sulfonyl]glycine,
12) N-[[4-[(Benzyloxymethylcarbonyl)amino]phenyl]sulfonyl]glycine,
13) N-[[4-(4-Methoxybenzoylamino)phenyl]sulfonyl]glycine,
14) N-[[4-(4-Fluorobenzoylamino)phenyl]sulfonyl]glycine,
15) N-[[4-(4-Nitrobenzoylamino)phenyl]sulfonyl]glycine,
16) N-[[4-(3-Nitrobenzoylamino)phenyl]sulfonyl]glycine,
17) N-[[4-(2-Nitrobenzoylamino)phenyl]sulfonyl]glycine,
18) N -[[4-(4-Formylbenzoylamino)phenyl]sulfonyl]glycine,
19) N-[[4-(Benzoylamino)phenyl]sulfonyl]-D-alpha-phenylglycine,
20) N-[[4-(Benzoylamino)phenyl]sulfonyl]-L-alpha-phenylglycine,
21) N-[[4-(4-Methylbenzoylamino)phenyl]sulfonyl]-D-alpha-phenylglycine,
22) N-[[4-(Methylbenzoylamino)phenyl]sulfonyl]-L-alpha-phenylglycine,
23) N-[[4-(4-Methoxybenzoylamino)phenyl]sulfonyl]-D-alpha-phenylglycine,
24) N-[[4-(4-Methoxybenzoylamino)phenyl]sulfonyl]-L-alpha-phenylglycine,
25) N-[[4-(4-Fluorobenzoylamino)phenyl]sulfonyl]-D-alpha-phenylglycine,
26) N-[[4-(4-Fluorobenzoylamino)phenyl]sulfonyl]-L-alpha-phenylglycine,
27) N-[[4-(4-Nitrobenzoylamino)phenyl]sulfonyl]-D-alpha-phenylglycine,
28) N-[[4-(4-Nitrobenzoylamino)phenyl]sulfonyl]-L-alpha-phenylglycine,
29) N -[(4-Pivaloyloxyphenyl)sulfonyl]-D,L-alpha-phenylglycine,
30) N-[(4-Pivaloyloxyphenyl)sulfonyl]-D,L-phenylalanine,
31) N-[[4-(2,4-Dichlorobenzoylamino)phenyl]sulfonyl]glycine,
32) N-[[4-(2,4-Dichlorobenzoylamino)phenyl]sulfonyl]-D,L-alanine,
33) N-[[4-(2,4-Dichlorobenzoylamino)phenyl]sulfonyl]-beta-alanine,
34) N-[[4-(2,4-Dichlorobenzoylamino)phenyl]sulfonyl]-L-valine,
35) N-[[4-(2,4-Dichlorobenzoylamino)phenyl]sulfonyl]-D,L-valine,
36) N-[[4-(2,4-Dichlorobenzoylamino)phenyl]sulfonyl]-L-leucine,
37) N-[[4-(2,4-Dichlorobenzoylamino)phenyl]sulfonyl]-D,L-leucine,
38) N-[[4-(2,4-Dichlorobenzoylamino)phenyl]sulfonyl]-D,L-serine,
39) N-[[4-(2,4-Dichlorobenzoylamino)phenyl]sulfonyl]-L-phenylalanine,
40) N-[[4-(2,4-Dichlorobenzoylamino)phenyl]sulfonyl]-L-tyrosine,
41) N-[[4-(2,4-Dichlorobenzoylamino)phenyl]sulfonyl]-D,L-alanine methyl ester,
42) N-[[4-(2,4-Dichlorobenzoylamino)phenyl]sulfonyl]-L-valine methyl ester,
43) N-[[4-(2,4-Dichlorobenzoylamino)phenyl]sulfonyl]-D,L-valine methyl ester,
44) N-[[4-(2,4-Dichlorobenzoylamino)phenyl]sulfonyl]-L-leucine methyl ester,
45) N-[[4-(2,4-Dichlorobenzoylamino)phenyl]sulfonyl]-D,L-serine methyl ester,
46) N-[[4-(2,4-Dichlorobenzoylamino)phenyl]sulfonyl]-L-tyrosine methyl ester,
47) N-[[4-(3-Nitrobenzoylamino)phenyl]sulfonyl]-L-aspartic acid,
48) N-[[3-(3-Nitrobenzoylamino)phenyl]sulfonyl]-L-aspartic acid,
49) N-[[4-(3-Aminobenzoylamino)phenyl]sulfonyl]-L-aspartic acid,
50) N-[[3-(3-Aminobenzoylamino)phenyl]sulfonyl]-L-aspartic acid,
51) N-[[4-(Benzoylamino)phenyl]sulfonyl]-L-glutamic acid,
52) N-[[4-(4-Chlorobenzoylamino)phenyl]sulfonyl]-L-glutamic acid,
53) N-[[4-(4-Nitrobenzoylamino)phenyl]sulfonyl]-L-glutamic acid,
54) N-[[4-[2-(4-(1-Pyrrolidinyl)phenyl]butyryloxy]phenyl]sulfonyl]-D,L-3-morpholinoalanine ethyl ester,
55) N-[[4-[2-(4-(1-Nitrophenyl)butyryloxy]phenyl]sulfonyl]-D,L-3-morpholinoalanine ethyl ester,
56) N-[[4-(2-Methoxy-2-phenylacetyloxy)phenyl]sulfonyl]-D,L-3-morpholinoalanine ethyl ester,
57) N-[[4-[[[1-(4-Nitrophenyl)cyclobutyl]carbonyl]oxy] phenyl]sulfonyl]-D,L-3-morpholinoalanine ethyl ester,
58) N-[[3-Methyl-4-[2-[4-(1-Pyrrolidinyl)phenyl]butyryloxy]phenyl]sulfonyl]-t-butoxycar-L-lysine,
59) N-[[4-(2-Phenylbutyryloxy)phenyl]sulfonyl]glycine,
60) N-[[4-[2-[4-(1-Pyrrolidinyl)phenyl]butyryloxy]phenyl] sulfonyl]-D,L-phenylalanine,
61) N-[[4-[2-[4-(1-Pyrrolidinyl)phenyl]butyryloxy]phenyl] sulfonyl]-D,L-aspartic acid,
62) N-[[4-[[[1-(4-Nitrophenyl)cyclobutyl]carbonyl]oxy] phenyl]sulfonyl]-D,L-aspartic acid,
63)1-[[4-[2-[4-(1-Pyrrolidinyl)phenyl]butyryloxy]phenyl] sulfonylamide]-1-cyclopropanecarboxylic acid,
64) N-[[4-[2-[4-(1-Pyrrolidinyl)phenyl]butyryloxy]phenyl] sulfonyl]-D,L-2-(2-furanyl)glycine,
65) N-[[4-[2-[4-(1-Pyrrolidinyl)phenyl]butyryloxy]phenyl] sulfonyl]-D,L-2-(2-tri-enyl)glycine,
66) N-[[4-[2-[4-(1-Pyrrolidinyl)phenyl]butyryloxy]phenyl] sulfonyl]-L-valine,
67) N-[[4-[2-[4-(1-Pyrrolidinyl)phenyl]butyryloxy]phenyl] sulfonyl]-S-carboxymethyl-L-cysteine,
68) N-[[4-[2-Ethyl-2-(4-methoxyphenyl)butyryloxy]phenyl]sulfonyl]-glycine,
69) N-[[3-Methyl-4-[2-[4-(1-Pyrrolidinyl)phenyl]butyryloxy]phenyl]sulfonyl]-L-lysine,
70) N-[[3 Methyl-4-[2-[4-(1-pyrrolidinyl)phenyl]butylyloxy]phenyl]sulfonyl]amino]pentanoic acid,
71) N-[[(3-Methyl-4-pivaloyloxy)phenyl]sulfonyl]-beta-alanine.

Purpose of the Invention

Bone is a metabolically active and highly organized connective tissue. The main functions of the bones are provision of mechanical and structural support, maintaining blood calcium levels, supporting haematopoiesis and housing the important vital organs such as brain, spinal cord and heart. To accomplish these functions bone needs continuous remodeling. Bone contains two distinct cell types, the osteoblasts, essential for bone formation (synthesis); and the osteoclasts, essential for bone resorption (break down). Morphogenesis and remodeling of bone involves the synthesis of bone matrix by osteoblasts and coordinated resorption by osteoclasts. The co-ordination between the osteoblasts and osteoclasts is very crucial in maintaining bone homeostasis and structural integrity of the skeleton. Both these processes are influenced by several hormones and local factors generated within bone and bone marrow, resulting in a complex network of control mechanisms. An imbalance of osteoblast and osteoclast functions can result in skeletal abnormalities characterized by increased or decreased bone mass. This may leads to excessive bone loss that reflects the balance of bone formation and bone resorption. Bone destruction or resorption is carried out by haematopoietically derived osteoclasts. Their number and activity is determined by cell lineage allocation, proliferation and differentiation of osteoclast precursors and the resorptive efficiency of mature osteoclasts. Important bone diseases such as osteoporosis, rheumatoid arthritis, Paget's disease of bone and bone metastasis of breast and prostate cancers are caused by increased osteoclast activity (Teitelbaum, 2000). In these disorders bone resorption exceeds bone formation resulting in decreased skeletal mass. This causes bones to become thin, fragile and susceptible to fracture. The consequences of osteoporotic bone fractures include chronic pain in bone, body deformity including height loss and muscle weakness. Therefore, to understand both pathogenesis and successful treatment of these bone diseases there is a need for better understanding of biology of osteoclasts.

Osteoporosis is now a serious problem that imposes substantial limitations on the affected individuals. In human, 1 in 3 women and 1 in 12 men over 45 years are at risk of suffering painful and deforming fractures as a result of osteoporosis. More women die after hip fractures than from cancers of ovaries, cervix and uterus. Osteoporosis occurs at a relatively earlier age in Indian males and females compared to western countries (Gupta, 1996). A variety of disadvantages are associated with current therapeutic agents used in osteoporosis and other metabolic bone disorders. The side effects of current therapies include increase in the risk of breast and uterine cancers, upper gastrointestinal distress and induction of immune responses. Drugs that inhibit the formation or activity of osteoclasts and with no toxicity and harmful side effects will be valuable for treating osteoporosis and other bone diseases. Bone resorption and loss of calcium from bone are complications associated with arthritis, many cancers and with bone metastases of breast and prostate tumors. Because of lack of research into osteoporosis and related diseases, we don't know all the answers to treat these diseases. Progress in better understanding the pathogenesis and successful treatment of these diseases to date has targeted osteoclast. Osteoclasts, the only cells capable of resorbing bone differentiate from the haemopoietic precursors of monocyte/macrophage lineage that also give rise to macrophages and dendritic cells (Miyamoto et al. 2001). Lineage choice and the differentiation process is guided by lineage restricted key regulatory molecules and transcription factors. Osteoclasts are large multinucleated cells. They are formed by the fusion of mononuclear cells of haemopoietic origin and not by mitosis, since DNA synthesis is not required. Osteoclast formation and bone resorption is regulated by many hormones, growth factors and immune cell-derived cytokines (Udagawa et al. 1995, Wani et al. 1999, Fox et al. 2000, Fuller et al. 2000). These factors act directly or indirectly via other cell types to influence osteoclast differentiation. The most important cell type influencing osteoclast formation is osteoblast, which promote this process by a contact-dependent mechanism. Recent advances revealed that two molecules, macrophage colony stimulating factor (M-CSF) and receptor activator of NF-κB ligand (RANKL) expressed by osteoblasts are essential and sufficient for the differentiation of haemopoietic cells to form osteoclasts (Tanaka et al. 1993, Anderson et al., 1997, Wong et al. 1997, Lacey et al. 1998, Yasuda et al. 1998). The precise role of other cells, such as T lymphocytes in bone homeostasis is yet to be fully elucidated. It has recently been reported that activated T cells regulates osteoclast formation by some unknown mechanisms. T cells support osteoclast formation by RANKL-dependent and RANKL-independent mechanisms (Weitzmann et al. 2001). Cytokines produced by activated T cells, as well as by other cell types regulates osteoclastogenesis in physiological and pathological conditions. Recent discovery of RANKL has enabled us for the meticulous dissection of mechanisms by which various factors regulate osteoclastogenesis, and better understanding of both pathogenesis and successful treatment bone diseases. In our preliminary studies, we have investigated the role of novel compounds on osteoclastogenesis induced by RANKL in the presence of M-CSF in stromal cell-free cultures of osteoclast precursors.

Natural products from plants and organisms have frequently been used as a source for development of effective drugs. There is an increased interest in analysis of natural products from marine organisms. Sea animals contain metabolites which can be used for treatment of many diseases.

The inventors have previously shown (US Patent #2003066083) that a novel extract (mussel hydrolysate) prepared from the Indian green mussel (*Perna viridis*) inhibits the osteoclast differentiation in murine haemopoietic precursors of monocyte/macrophage cell lineage. The extract also inhibits the bone resorbing activity of osteoclasts. There was approximately 80-90% inhibition of osteoclast formation and bone resorption in the presence of extract. More importantly, the extract is non-toxic to other cells and is useful to prepare a drug for the treatment of osteoporosis and other bone diseases.

In further investigation, at each stages of purification we found a significant inhibition of osteoclast formation and bone resorption (60-90%). We have purified some active components from extract and these active components significantly inhibit both osteoclast formation and bone resorption. These active compounds can be used in therapeutic settings to protect and cure the individuals against osteoporosis and other metabolic bone diseases.

The current known therapeutic agents have a variety of associated disadvantages. The side effects of current therapies include an elevated risk of breast and uterine cancers, upper gastrointestinal distress and induction of immune responses (Watts' 1999). Our earlier US Patent (#2003066083) describes preparation of mussell hydrolysate from the Indian green mussel (*Perna viridis*) and its inhibition of the osteoclast differentiation in murine hemopoietic precursors of monocyte/macrophage cell lineage. The extract also shows inhibition of the bone resorbing activity of osteoclasts.

The present inventors have found that a series of novel sulfonic acid/sulfate derivatives of acidic amino acids, aspartic acids, glutamic acid, homoglutamic acid and their related aliphatic dicarboxylic acids (Succinic acid, glutaric acid and adipic acid) have inhibitory activity against osteoclast formation and bone resorption. These compounds are novel and non-toxic to other cells. The active compounds may play a vital role in inhibition of differentiation of osteoclast from hemopoietic precursors and can be used in therapeutic settings to protect and cure the individuals against osteoporosis and other metabolic bone diseases.

SUMMARY OF THE INVENTION

This invention relates to a novel class of acidic amino acid/dicarboxylic acid derivatives (sulfonic acid/sulfate derivatives of naturally occurring amino acids and their amides) useful as inhibitors of osteoclastogenesis. The invention also provides methods of using the novel class of acidic amino acid/dicarboxylic acid derivatives of the general formula ZOC—(CRR)$_m$—COOH, wherein: m=2, 3 or 4; Z is OH or NH$_2$; one R in the composition is from the group consisting of SO$_3$H, OSO$_3$H, CH$_2$—SO$_3$H, CH$_2$—OSO$_3$H, and NHSO$_3$H, and the remaining Rs are H or NH$_2$. Thus, the compounds may bear the general formula ZOC—CR$_7$R$_8$—CR$_5$R$_6$—CR$_3$R$_4$—CR$_1$R$_2$—COOH, ZOC—CR$_5$R$_6$—CR$_3$R$_4$—CR$_1$R$_2$—COOH or ZOC—CR$_3$R$_4$—CR$_1$R$_2$—COOH wherein Z is OH or NH$_2$, and R$_1$ to R$_8$ denotes H, NH$_2$, SO$_3$H, or OSO$_3$H, CH$_2$—SO$_3$H, CH$_2$—OSO$_3$H, NHSO$_3$H. Mixtures of these compounds may be administered, as well.

DETAILED DESCRIPTION OF THE INVENTION

The present invention is related to:

A) Osteoclast inhibitors containing novel class of acidic amino acid/dicarboxylic acid derivatives (sulfonic acid/sulfate derivatives of naturally occurring amino acids and their amides);

B) Osteoclast inhibitors containing novel class of acidic amino acid/dicarboxylic acid derivatives of the general formula ZOC—(CRR)$_m$—COOH, wherein: m=2, 3 or 4; Z is OH or NH$_2$; one R in the composition is from the group consisting of SO$_3$H, OSO$_3$H, CH$_2$—SO$_3$H, CH$_2$—OSO$_3$H, and NHSO$_3$H, and the remaining Rs are H or NH$_2$. Thus, compounds may bear the general formula:

   (Ia)

ZOC—CR$_3$R$_4$—CR$_1$R$_2$—COOH

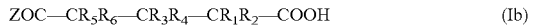   (Ib)

ZOC—CR$_5$R$_6$—CR$_3$R$_4$—CR$_1$R$_2$—COOH

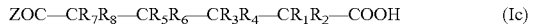   (Ic)

ZOC—CR$_7$R$_8$—CR$_5$R$_6$—CR$_3$R$_4$—CR$_1$R$_2$—COOH wherein:
Z is OH or NH$_2$; and
R$_1$ to R$_8$ are H, NH$_2$, SO$_3$H or OSO$_3$H, CH$_2$—SO$_3$H, CH$_2$—OSO$_3$H, NHSO$_3$H. And this includes the following class of compounds:

1. A compound in which Z=OH, R$_1$=NHSO$_3$H, R$_2$=R$_3$=R$_4$=H is the same meaning as hereinbefore defined;
2. A compound in which Z=OH, R$_1$=NH$_2$, R$_3$=R$_4$=H, R$_2$=SO$_3$H is the same meaning as hereinbefore defined;
3. A compound in which Z=OH, R$_1$=NH$_2$, R$_3$=R$_4$=H, R$_2$=OSO$_3$H is the same meaning as hereinbefore defined;
4. A compound in which Z=OH, R$_1$=NH$_2$, R$_2$=R$_4$=H, R$_3$=SO$_3$H is the same meaning as hereinbefore defined;
5. A compound in which Z=OH, R$_1$=NH$_2$, R$_2$=R$_4$=H, R$_3$=OSO$_3$H is the same meaning as hereinbefore defined;
6. A compound in which Z=OH, R$_1$=NH$_2$, R$_2$=R$_3$=H, R$_4$=SO$_3$H is the same meaning as hereinbefore defined;
7. A compound in which Z=OH, R$_1$=NH$_2$, R$_2$=R$_3$=H, R$_4$=OSO$_3$H is the same meaning as hereinbefore defined;
8. A compound in which Z=OH, R$_1$=R$_3$=R$_4$=H, R$_2$=CH$_2$SO$_3$H is the same meaning as hereinbefore defined;
9. A compound in which Z=OH, R$_1$=R$_3$=R$_4$=H, R$_2$=CH$_2$OSO$_3$H is the same meaning as hereinbefore defined;
10. A compound in which Z=OH, R$_1$=R$_3$=R$_4$=H, R$_2$=SO$_3$H is the same meaning as hereinbefore defined;
11. A compound in which Z=OH, R$_1$=R$_3$=R$_4$=H, R$_2$=OSO$_3$H is the same meaning as hereinbefore defined;
12. A compound in which Z=OH, R$_2$=NHSO$_3$H, R$_1$=R$_3$=R$_4$=H is the same meaning as hereinbefore defined;
13. A compound in which Z=OH, R$_2$=H, R$_1$=CH$_2$SO$_3$H is the same meaning as hereinbefore defined;
14. A compound in which Z=OH, R$_2$=H, R$_1$=CH$_2$OSO$_3$H is the same meaning as hereinbefore defined;
15. A compound in which Z=OH, R$_2$=H, R$_1$=SO$_3$H is the same meaning as hereinbefore defined;
16. A compound in which Z=OH, R$_2$=H, R$_1$=OSO$_3$H is the same meaning as hereinbefore defined;
17. A compound in which Z=OH, R$_2$=NH$_2$, R$_3$=R$_4$=H, R$_1$=SO$_3$H is the same meaning as hereinbefore defined;
18. A compound in which Z=OH, R$_2$=NH$_2$, R$_3$=R$_4$=H, R$_1$=SO$_3$H is the same meaning as hereinbefore defined;
19. A compound in which Z=OH, R$_2$=NH$_2$, R$_1$=R$_4$=H, R$_3$=SO$_3$H is the same meaning as hereinbefore defined;
20. A compound in which Z=OH, R$_2$=NH$_2$, R=R$_4$=H, R$_3$=OSO$_3$H is the same meaning as hereinbefore defined;
21. A compound in which Z=OH, R$_2$=NH$_2$, R$_1$=R$_3$=H, R$_4$=SO$_3$H is the same meaning as hereinbefore defined;
22. A compound in which Z=OH, R$_2$=NH$_2$, R$_1$=R$_3$=H, R$_4$=OSO$_3$H is the same meaning as hereinbefore defined;
23. A compound in which R$_1$=NHSO$_3$H, R$_2$=R$_3$=R$_4$=H is the same meaning as hereinbefore defined;
24. A compound in which Z=NH$_2$, R$_1$=H, R$_2$=CH$_2$SO$_3$H is the same meaning as hereinbefore defined;
25. A compound in which Z=NH$_2$, R$_1$=H, R$_2$=CH$_2$OSO$_3$H is the same meaning as hereinbefore defined;
26. A compound in which Z=NH$_2$, R$_1$=H, R$_2$=SO$_3$H is the same meaning as hereinbefore defined;
27. A compound in which Z=NH$_2$, R$_1$=H, R$_2$=OSO$_3$H is the same meaning as hereinbefore defined;
28. A compound in which Z=R$_1$=NH$_2$, R$_2$=R$_4$=H, R$_2$=SO$_3$H is the same meaning as hereinbefore defined;
29. A compound in which Z=R$_1$=NH$_2$, R$_2$=R$_4$=H, R$_3$=OSO$_3$H is the same meaning as hereinbefore defined;
30. A compound in which Z=R$_1$=NH$_2$, R$_2$=R$_4$=H, R$_3$=SO$_3$H is the same meaning as hereinbefore defined;
31. A compound in which Z=R$_1$=NH$_2$, R$_2$=R$_4$=H, R$_3$=OSO$_3$H is the same meaning as hereinbefore defined;
32. A compound in which Z=R$_1$=NH$_2$, R$_2$=R$_3$=H, R$_4$=SO$_3$H is the same meaning as hereinbefore defined;
33. A compound in which Z=R$_1$=NH$_2$, R$_2$=R$_3$=H, R$_4$=OSO$_3$H is the same meaning as hereinbefore defined;

34. A compound in which Z=NH$_2$, R$_2$=NHSO$_3$H, R$_1$=R$_3$=R$_4$=H is the same meaning as hereinbefore defined;

35. A compound in which Z=NH$_2$, R$_2$ to R$_4$=H, R$_1$=CH$_2$SO$_3$H is the same meaning as hereinbefore defined;

36. A compound in which Z=NH$_2$, R$_2$ to R$_4$=H, R$_1$=CH$_2$SO$_3$H is the same meaning as hereinbefore defined;

37. A compound in which Z=OH, R$_2$ to R$_4$=H, R$_1$=SO$_3$H is the same meaning as hereinbefore defined;

38. A compound in which Z=OH, R$_2$ to R$_4$=H, R$_1$=OSO$_3$H is the same meaning as hereinbefore defined;

39. A compound in which Z=R$_2$=NH$_2$, R$_3$=R$_4$=H, R$_1$=SO$_3$H is the same meaning as hereinbefore defined;

40. A compound in which Z=R$_2$=NH$_2$, R$_3$=R$_4$=H, R$_1$=OSO$_3$H is the same meaning as hereinbefore defined;

41. A compound in which Z=R$_2$=NH$_2$, R$_1$=R$_4$=H, R$_3$=SO$_3$H is the same meaning as hereinbefore defined;

42. A compound in which Z=R$_2$=NH$_2$, R$_1$=R$_4$=H, R$_3$=OSO$_3$H is the same meaning as hereinbefore defined;

43. A compound in which Z=R$_2$=NH$_2$, R$_1$=R$_3$=H, R$_4$=SO$_3$H is the same meaning as hereinbefore defined;

44. A compound in which Z=R$_2$=NH$_2$, R$_1$=R$_3$=H, R$_4$=OSO$_3$H is the same meaning as hereinbefore defined;

45. A compound in which Z=OH, R$_1$=NHSO$_3$H, R$_2$=R$_3$=R$_4$=R$_5$=R$_6$=H is the same meaning as hereinbefore defined;

46. A compound in which Z=OH, R$_1$, R$_3$ to R$_6$=H, R$_2$=CH$_2$SO$_3$H is the same meaning as hereinbefore defined;

47. A compound in which Z=OH, R$_1$, R$_3$ to R$_6$=H, R$_2$=CH$_2$OSO$_3$H is the same meaning as hereinbefore defined;

48. A compound in which Z=OH, R$_1$, R$_3$ to R$_6$=H, R$_2$=SO$_3$H is the same meaning as hereinbefore defined;

49. A compound in which Z=OH, R$_1$, R$_3$ to R$_6$=H, R$_2$=OSO$_3$H is the same meaning as hereinbefore defined;

50. A compound in which Z=OH, R$_2$ to R$_6$=H, R$_1$=OSO$_3$H is the same meaning as hereinbefore defined;

51. A compound in which Z=OH, R$_2$ to R$_6$=H, R$_1$=SO$_3$H is the same meaning as hereinbefore defined;

52. A compound in which Z=OH, R$_1$=NH$_2$, R$_3$ to R$_6$=H, R$_2$=SO$_3$H is the same meaning as hereinbefore defined;

53. A compound in which Z=OH, R$_1$=NH$_2$, R$_3$ to &=H, R$_2$=OSO$_3$H is the same meaning as hereinbefore defined;

54. A compound in which Z=OH, R$_1$=NH$_2$, R$_2$=H, R$_4$ to R$_6$=H, R$_3$=SO$_3$H is the same meaning as hereinbefore defined;

55. A compound in which Z=OH, R$_1$=NH$_2$, R$_2$=H, R$_4$ to R$_6$=H, R$_3$=OSO$_3$H is the same meaning as hereinbefore defined;

56. A compound in which Z=OH, R$_1$=NH$_2$, R$_2$=R$_3$=R$_5$=R$_6$=H, R$_4$=SO$_3$H is the same meaning as hereinbefore defined;

57. A compound in which Z=OH, R$_1$=NH$_2$, R$_2$=R$_3$=R$_5$=R$_6$=H, R$_4$=OSO$_3$H is the same meaning as hereinbefore defined;

58. A compound in which Z=OH, R$_1$=NH$_2$, R$_2$=R$_3$=R$_4$=R$_6$=H, R$_5$=SO$_3$H is the same meaning as hereinbefore defined;

59. A compound in which Z=OH, R$_1$=NH$_2$, R$_2$=R$_3$=R$_4$=R$_6$=H, R$_5$=OSO$_3$H is the same meaning as hereinbefore defined;

60. A compound in which Z=OH, R$_1$=NH$_2$, R$_2$ to R$_5$=H, R$_6$=SO$_3$H is the same meaning as hereinbefore defined;

61. A compound in which Z=OH, R$_1$=NH$_2$, R$_2$ to R$_5$=H, R$_6$=OSO$_3$H is the same meaning as hereinbefore defined;

62. A compound in which Z=OH, R$_2$=NHSO$_3$H, R$_1$, R$_3$ to R$_6$=H is the same meaning as hereinbefore defined;

63. A compound in which Z=OH, R$_2$ to R$_6$=H, R$_1$=CH$_2$SO$_3$H is the same meaning as hereinbefore defined;

64. A compound in which Z=OH, R$_2$ to R$_6$=H, R$_1$=CH$_2$OSO$_3$H is the same meaning as hereinbefore defined;

65. A compound in which Z=OH, R$_2$=NH$_2$, R$_3$ to R$_6$H, R$_1$=SO$_3$H is the same meaning as hereinbefore defined;

66. A compound in which Z=OH, R$_2$=NH$_2$, R$_3$ to R$_6$H, R$_1$=OSO$_3$H is the same meaning as hereinbefore defined;

67. A compound in which Z=OH, R$_2$=NH$_2$, R$_1$, R$_4$ to R$_6$H, R$_3$=SO$_3$H is the same meaning as hereinbefore defined;

68. A compound in which Z=OH, R$_2$=NH$_2$, R$_1$, R$_4$ to R$_6$H, R$_3$=OSO$_3$H is the same meaning as hereinbefore defined;

69. A compound in which Z=OH, R$_2$=NH$_2$, R$_1$=R$_3$=R$_5$=R$_6$=H, R$_4$=SO$_3$H is the same meaning as hereinbefore defined;

70. A compound in which Z=OH, R$_2$=NH$_2$, R$_1$=R$_3$=R$_5$=R$_6$=H, R$_4$=OSO$_3$H is the same meaning as hereinbefore defined;

71. A compound in which Z=OH, R$_2$=NH$_2$, R$_1$=R$_3$=R$_4$=R$_6$=H, R$_5$=SO$_3$H is the same meaning as hereinbefore defined;

72. A compound in which Z=OH, R$_2$=NH$_2$, R$_1$=R$_3$=R$_4$=R$_6$=H, R$_5$=OSO$_3$H is the same meaning as hereinbefore defined;

73. A compound in which Z=OH, R$_2$=NH$_2$, R$_1$=R$_3$=R$_4$=R$_5$=H, R$_6$=SO$_3$H is the same meaning as hereinbefore defined;

74. A compound in which Z=OH, R$_2$=NH$_2$, R$_1$=R$_3$=R$_4$=R$_5$=H, R$_6$=OSO$_3$H is the same meaning as hereinbefore defined;

75. A compound in which Z=NH$_2$, R$_1$=NHSO$_3$H, R$_2$ to R$_6$=H is the same meaning as hereinbefore defined;

76. A compound in which Z=R$_1$=NH$_2$, R$_3$ to R$_6$=H, R$_2$=SO$_3$H is the same meaning as hereinbefore defined;

77. A compound in which Z=R$_1$=NH$_2$, R$_3$ to R$_6$=H, R$_2$=OSO$_3$H is the same meaning as hereinbefore defined;

78. A compound in which Z=R$_1$=NH$_2$, R$_2$=H, R$_4$ to R$_6$=H, R$_3$=SO$_3$H is the same meaning as hereinbefore defined;

79. A compound in which Z=R$_1$=NH$_2$, R$_2$=H, R$_3$ to R$_6$=H, R$_3$=OSO$_3$H is the same meaning as hereinbefore defined;

80. A compound in which Z=R$_1$=NH$_2$, R$_2$=R$_3$=R$_5$=R$_6$=H, R$_4$=SO$_3$H is the same meaning as hereinbefore defined;

81. A compound in which Z=R$_1$=NH$_2$, R$_2$=R$_3$=R$_5$=R$_6$=H, R$_4$=OSO$_3$H is the same meaning as hereinbefore defined;

82. A compound in which $Z=R_1=NH_2$, $R_2=R_3=R_4=R_6=H$, $R_5=SO_3H$ is the same meaning as hereinbefore defined;
83. A compound in which $Z=R_1=NH_2$, $R_2=R_3=R_4=R_6=H$, $R_5=OSO_3H$ is the same meaning as hereinbefore defined;
84. A compound in which $Z=R_1=NH_2$, $R_2$ to $R_5=H$, $R_6=SO_3H$ is the same meaning as hereinbefore defined;
85. A compound in which $Z=R_1=NH_2$, $R_2$ to $R_5=H$, $R_6=OSO_3H$ is the same meaning as hereinbefore defined;
86. A compound in which $Z=NH_2$, $R_1$, $R_3$ to $R_6=H$, $R_2=CH_2SO_3H$ is the same meaning as hereinbefore defined;
87. A compound in which $Z=NH_2$, $R_1$, $R_3$ to $R_6=H$, $R_2=CH_2OSO_3H$ is the same meaning as hereinbefore defined;
88. A compound in which $Z=NH_2$, $R_1$, $R_3$ to $R_6=H$, $R_2=SO_3H$ is the same meaning as hereinbefore defined;
89. A compound in which $Z=NH_2$, $R_1$, $R_3$ to $R_6=H$, $R_2=OSO_3H$ is the same meaning as hereinbefore defined;
90. A compound in which $Z=NH_2$, $R_2$ to $R_6=H$, $R_1=OSO_3H$ is the same meaning as hereinbefore defined;
91. A compound in which $Z=NH_2$, $R_2$ to $R_6=H$, $R_1=SO_3H$ is the same meaning as hereinbefore defined;
92. A compound in which $Z=NH_2$, $R_2=NHSO_3H$; $R_1=H$, $R_3$ to $R_6=H$ is the same meaning as hereinbefore defined;
93. A compound in which $Z=NH_2$, $R_2$ to $R_6=H$, $R_1=CH_2SO_3H$ is the same meaning as hereinbefore defined;
94. A compound in which $Z=NH_2$, $R_2$ to $R_6=H$, $R_1=CH_2OSO_3H$ is the same meaning as hereinbefore defined;
95. A compound in which $Z=NH_2$, $R_2=NH_2$, $R_3$ to $R_6=H$, $R_1=SO_3H$ is the same meaning as hereinbefore defined;
96. A compound in which $Z=NH_2$, $R_2=NH_2$, $R_3$ to $R_6=H$, $R_1=OSO_3H$ is the same meaning as hereinbefore defined;
97. A compound in which $Z=NH_2$, $R_2=NH_2$, $R_1$, $R_4$ to $R_6H$, $R_3=SO_3H$ is the same meaning as hereinbefore defined;
98. A compound in which $Z=R_2=NH_2$, $R_1$, $R_4$ to & H, $R_3=OSO_3H$ is the same meaning as hereinbefore defined;
99. A compound in which $Z=R_2=NH_2$, $R_1=R_3=R_5=R_6=H$, $R_4=SO_3H$ is the same meaning as hereinbefore defined;
100. A compound in which $Z=R_2=NH_2$, $R_1=R_3=R_5=R_6=H$, $R_4=OSO_3H$ is the same meaning as hereinbefore defined;
101. A compound in which $Z=R_2=NH_2$, $R_1=R_3=R_4=R_6=H$, $R_5=SO_3H$ is the same meaning as hereinbefore defined;
102. A compound in which $Z=R_2=NH_2$, $R_1=R_3=R_4=R_6=H$, $R_5=OSO_3H$ is the same meaning as hereinbefore defined;
103. A compound in which $Z=R_2=NH_2$, $R_1=R_3=R_4=R_5=H$, $R_6=SO_3H$ is the same meaning as hereinbefore defined;
104. A compound in which $Z=R_2=NH_2$, $R_1=R_3=R_4=R_5=H$, $R_6=OSO_3H$ is the same meaning as hereinbefore defined;
105. A compound in which $Z=OH$, $R_1=NHSO_3H$, $R_2$ to $R_8=H$ is the same meaning as hereinbefore defined;
106. A compound in which $Z=OH$, $R_1$, $R_3$ to $R_8=H$, $R_2=CH_2SO_3H$ is the same meaning as hereinbefore defined;
107. A compound in which $Z=OH$, $R_1$, $R_3$ to $R_8=H$, $R_2=CH_2OSO_3H$ is the same meaning as hereinbefore defined;
108. A compound in which $Z=OH$, $R_1$, $R_3$ to $R_8=H$, $R_2=SO_3H$ is the same meaning as hereinbefore defined;
109. A compound in which $Z=OH$, $R_1$, $R_3$ to $R_8=H$, $R_2=OSO_3H$ is the same meaning as hereinbefore defined;
110. A compound in which $Z=OH$, $R_1=NH_2$, $R_3$ to $R_8=H$, $R_2=SO_3H$ is the same meaning as hereinbefore defined;
111. A compound in which $Z=OH$, $R_1=NH_2$, $R_3$ to $R_8=H$, $R_2=OSO_3H$ is the same meaning as hereinbefore defined;
112. A compound in which $Z=OH$, $R_1=NH_2$, $R_2=H$, $R_4$ to $R_8=H$, $R_3=SO_3H$ is the same meaning as hereinbefore defined;
113. A compound in which $Z=OH$, $R_1=NH_2$, $R_2=H$, $R_4$ to $R_8=H$, $R_3=OSO_3H$ is the same meaning as hereinbefore defined;
114. A compound in which $Z=OH$, $R_1=NH_2$, $R_2=R_3=H$, $R_5$ to $R_8=H$, $R_4=SO_3H$ is the same meaning as hereinbefore defined;
115. A compound in which $Z=OH$, $R_1=NH_2$, $R_2=R_3=H$, $R_5$ to $R_8=H$, $R_4=OSO_3H$ is the same meaning as hereinbefore defined;
116. A compound in which $Z=OH$, $R_1=NH_2$, $R_2=R_3=R_4=H$, $R_6$ to $R_8=H$, $R_5=SO_3H$ is the same meaning as hereinbefore defined;
117. A compound in which $Z=OH$, $R_1=NH_2$, $R_2=R_3=R_4=H$, $R_6$ to $R_8=H$, $R_5=OSO_3H$ is the same meaning as hereinbefore defined;
118. A compound in which $Z=OH$, $R_1=N-H_2$, $R_2=R_5=H$, $R_7=R_8=H$, $R_6=SO_3H$ is the same meaning as hereinbefore defined;
119. A compound in which $Z=OH$, $R_1=NH_2$, $R_2=R_5=H$, $R_7=R_8=H$, $R_6=OSO_3H$ is the same meaning as hereinbefore defined;
120. A compound in which $Z=OH$, $R_1=NH_2$, $R_2$ to $R_6=H$, $R_8=H$, $R_7=SO_3H$ is the same meaning as is before defined;
121. A compound in which $Z=OH$, $R_1=NH_2$, $R_2$ to $R_6=H$, $R_8=H$, $R_7=OSO_3H$ is the same meaning as hereinbefore defined;
122. A compound in which $Z=OH$, $R_1=NH_2$, $R_2$ to $R_7=H$, $R_8=SO_3H$ is the same meaning as hereinbefore defined;
123. A compound in which $Z=OH$, $R_1=NH_2$, $R_2$ to $R_7=H$, $R_8=OSO_3H$ is the same meaning as hereinbefore defined;
124. A compound in which $Z=OH$, $R_2=NHSO_3H$, $R_1$, $R_3$ to $R_8=H$ is the same meaning as hereinbefore defined;
125. A compound in which $Z=OH$, $R_2$ to $R_8=H$, $R_1=CH_2SO_3H$ is the same meaning as hereinbefore defined;
126. A compound in which $Z=OH$, $R_2$ to $R_8=H$, $R_1=CH_2OSO_3H$ is the same meaning as hereinbefore defined;
127. A compound in which $Z=OH$, $R_2$ to $R_8=H$, $R_1=SO_3H$ is the same meaning as hereinbefore defined;
128. A compound in which $Z=OH$, $R_2$ to $R_8=H$, $R_1=OSO_3H$ is the same meaning as hereinbefore defined;
129. A compound in which $Z=OH$, $R_2=NH_2$, $R_3$ to $R_8=H$, $R_1=SO_3H$ is the same meaning as hereinbefore defined;

130. A compound in which $Z=OH$, $R_2=NH_2$, $R_3$ to $R_8=H$, $R_1=OSO_3H$ is the same meaning as hereinbefore defined;

131. A compound in which $Z=OH$, $R_2=NH_2$, $R_1$, $R_4$ to $R_8=H$, $R_3=SO_3H$ is the same meaning as hereinbefore defined;

132. A compound in which $Z=OH$, $R_2=NH_2$, $R_1$, $R_4$ to $R_8=H$, $R_3=OSO_3H$ is the same meaning as hereinbefore defined;

133. A compound in which $Z=OH$, $R_2=NH_2$, $R_1=R_3=H$, $R_5$ to $R_8=H$, $R_4=SO_3H$ is the same meaning as hereinbefore defined;

134. A compound in which $Z=OH$, $R_2=NH_2$, $R_1=R_3=H$, $R_5$ to $R_8=H$, $R_4=OSO_3H$ is the same meaning as hereinbefore defined;

135. A compound in which $Z=OH$, $R_2=NH_2$, $R_1=R_3=R_4=H$, $R_6$ to $R_8=H$, $R_5=SO_3H$ is the same meaning as is before defined;

136. A compound in which $Z=OH$, $R_2=NH_2$, $R_1=R_3=R_4=H$, $R_6$ to $R_8=H$, $R_5=OSO_3H$ is the same meaning as hereinbefore defined;

137. A compound in which $Z=OH$, $R_2=NH_2$, $R_1=H$, $R_3$ to $R_5=H$, $R_7=R_8=H$, $R_6=SO_3H$ is the same meaning as hereinbefore defined;

138. A compound in which $Z=OH$, $R_2=NH_2$, $R_1=H$, $R_3$ to $R_5=H$, $R_7=R_8=H$, $R_6=OSO_3H$ is the same meaning as hereinbefore defined;

139. A compound in which $Z=OH$, $R_2=NH_2$, $R_1=R_8=H$, $R_3$ to $R_6=H$, $R_7=SO_3H$ is the same meaning as hereinbefore defined;

140. A compound in which $Z=OH$, $R_2=NH_2$, $R_1=R_8=H$, $R_3$ to $R_6=H$, $R_7=OSO_3H$ is the same meaning as hereinbefore defined;

141. A compound in which $Z=OH$, $R_2=NH_2$, $R_1=H$, $R_3$ to $R_7=H$, $R_8=SO_3H$ is the same meaning as hereinbefore defined;

142. A compound in which $Z=OH$, $R_2=NH_2$, $R_1=H$, $R_3$ to $R_7=H$, $R_8=OSO_3H$ is the same meaning as hereinbefore defined;

143. A compound in which $Z=NH_2$, $R_1=NHSO_3H$, $R_2$ to $R_8=H$ is the same meaning as hereinbefore defined;

144. A compound in which $Z=NH_2$, $R_1$ and $R_3$ to $R_8=H$, $R_2=CH_2SO_3H$ is the same meaning as hereinbefore defined;

145. A compound in which $Z=NH_2$, $R_1$ and $R_3$ to $R_8=H$, $R_2=CH_2OSO_3H$ is the same meaning as hereinbefore defined;

146. A compound in which $Z=NH_2$, $R_1$ and $R_3$ to $R_8=H$, $R_2=SO_3H$ is the same meaning as hereinbefore defined;

147. A compound in which $Z=NH_2$, $R_1$ and $R_3$ to $R_8=H$, $R_2=OSO_3H$ is the same meaning as hereinbefore defined;

148. A compound in which $Z=R_1=NH_2$, $R_3$ to $R_8=H$, $R_2=SO_3H$ is the same meaning as hereinbefore defined;

149. A compound in which $Z=R_1=NH_2$, $R_3$ to $R_8=H$, $R_2=OSO_3H$ is the same meaning as hereinbefore defined;

150. A compound in which $Z=R_1=NH_2$, $R_2=H$, $R_4$ to $R_8=H$, $R_3=SO_3H$ is the same meaning as hereinbefore defined;

151. A compound in which $Z=R_1=NH_2$, $R_2=H$, $R_4$ to $R_8=H$, $R_3=OSO_3H$ is the same meaning as hereinbefore defined;

152. A compound in which $Z=R_1=NH_2$, $R_2=R_3=H$, $R_5$ to $R_8=H$, $R_4=SO_3H$ is the same meaning as hereinbefore defined;

153. A compound in which $Z=R_1=NH_2$, $R_2=R_3=H$, $R_5$ to $R_8=H$, $R_4=OSO_3H$ is the same meaning as hereinbefore defined;

154. A compound in which $Z=R_1=NH_2$, $R_2=R_3=R_4=H$, $R_6$ to $R_8=H$, $R_5=SO_3H$ is the same meaning as hereinbefore defined;

155. A compound in which $Z=R_1=NH_2$, $R_2=R_3=R_4=H$, $R_6$ to $R_8=H$, $R_5=OSO_3H$ is the same meaning as hereinbefore defined;

156. A compound in which $Z=R_1=NH_2$, $R_2=R_5=H$, $R_7=R_8=H$, $R_6=SO_3H$ is the same meaning as hereinbefore defined;

157. A compound in which $Z=R_1=NH_2$, $R_2=R_5=H$, $R_7=R_8=H$, $R_6=OSO_3H$ is the same meaning as hereinbefore defined;

158. A compound in which $Z=R_1=NH_2$, $R_2$ to $R_6=H$, $R_8=H$, $R_7=SO_3H$ is the same meaning as hereinbefore defined;

159. A compound in which $Z=R_1=NH_2$, $R_2$ to $R_6=H$, $R_8=H$, $R_7=OSO_3H$ is the same meaning as hereinbefore defined;

160. A compound in which $Z=R_1=NH_2$, $R_2$ to $R_7=H$, $R_8=SO_3H$ is the same meaning as hereinbefore defined;

161. A compound in which $Z=R_1=NH_2$, $R_2$ to $R_7=H$, $R_8=OSO_3H$ is the same meaning as hereinbefore defined;

162. A compound in which $Z=NH_2$, $R_2=NHSO_3H$, $R_1$ and $R_3$ to $R_8=H$ is the same meaning as hereinbefore defined;

163. A compound in which $Z=NH_2$, $R_2$ to $R_8=H$, $R_1=CH_2SO_3H$ is the same meaning as hereinbefore defined;

164. A compound in which $Z=NH_2$, $R_2$ to $R_8=H$, $R_1=CH_2OSO_3H$ is the same meaning as hereinbefore defined;

165. A compound in which $Z=NH_2$, $R_2$ to $R_8=H$, $R_1=SO_3H$ is the same meaning as hereinbefore defined;

166. A compound in which $Z=NH_2$, $R_2$ to $R_8=H$, $R_1=OSO_3H$ is the same meaning as hereinbefore defined;

167. A compound in which $Z=R_2=NH_2$, $R_3$ to $R_8=H$, $R_1=SO_3H$ is the same meaning as hereinbefore defined;

168. A compound in which $Z=R_2=NH_2$, $R_3$ to $R_8=H$, $R_1=OSO_3H$ is the same meaning as hereinbefore defined;

169. A compound in which $Z=R_2=NH_2$, $R_1$, $R_4$ to $R_8=H$, $R_3=SO_3H$ is the same meaning as hereinbefore defined;

170. A compound in which $Z=R_2=NH_2$, $R_1$, $R_4$ to $R_8=H$, $R_3=OSO_3H$ is the same meaning as hereinbefore defined;

171. A compound in which $Z=R_2=NH_2$, $R_1=R_3=H$, $R_5$ to $R_8=H$, $R_4=SO_3H$ is the same meaning as hereinbefore defined;

172. A compound in which $Z=R_2=NH_2$, $R_1=R_3=H$, $R_5$ to $R_8=H$, $R_4=OSO_3H$ is the same meaning as hereinbefore defined;

173. A compound in which $Z=R_2=NH_2$, $R_1=R_3=R_4=H$, $R_6$ to $R_8=H$, $R_5=SO_3H$ is the same meaning as hereinbefore defined;

174. A compound in which $Z=R_2=NH_2$, $R_1=R_3=R_4=H$, $R_6$ to $R_8=H$, $R_5=OSO_3H$ is the same meaning as hereinbefore defined;

175. A compound in which $Z=R_2=NH_2$, $R_1=H$, $R_3$ to $R_5=H$, $R_7=R_8=H$, $R_6=SO_3H$ is the same meaning as hereinbefore defined;

176. A compound in which $Z=R_2=NH_2$, $R_1=H$, $R_3$ to $R_5=H$, $R_7=R_8=H$, $R_6=OSO_3H$ is the same meaning as hereinbefore defined;

177. A compound in which Z=R$_2$=NH$_2$, R$_1$=R$_8$=H, R$_3$ to R$_6$=H, R$_7$=SO$_3$H is the same meaning as hereinbefore defined;

178. A compound in which Z=R$_2$=NH$_2$, R$_1$=R$_8$=H, R$_3$ to R$_6$=H, R$_7$=OSO$_3$H is the same meaning as hereinbefore defined;

179. A compound in which Z=R$_2$=NH$_2$, R$_1$=H, R$_3$ to R$_7$=H, R$_8$=SO$_3$H is the same meaning as hereinbefore defined;

180. A compound in which Z=R$_2$=NH$_2$, R$_1$=H, R$_3$ to R$_7$=H, R$_8$=OSO$_3$H is the same meaning as hereinbefore defined.

C) The osteoclast inhibitors also contained different divalent metal ions such as Mg, Ca and Zn. The composition consisted of varying amounts of the above acid amino acid/dicarboxylic acid derivatives and their pharmaceutically acceptable salts. Non toxic salts of the present invention are contained all pharmaceutically acceptable salts, for example, general salts, acid addition salt, hydrate salts.

The compounds of the formulae (Ia), (Ib) and (Ic) of the present invention may be converted into the corresponding salts. Non toxic and water soluble salts are preferable. Suitable salts for example are as follows:

Salts of alkaline earth metals (Mg, Ca etc)
Ammonium Salts
Salts of pharmaceutically acceptable organic amines (tetramethyl ammonium, triethyl amine, methyl amine, cyclopentyl amine, benzylamine, phenethylamine, piperidine, monoethanolamine, diethanolamine, tris(hydroxymethyl)amine, lysine, arginine, N-methyl glucamine, etc.

d) In the compound of the present invention of the formulae (Ia), (Ib) and (Ic) the following non toxic derivatives thereof are preferable:

1. L-Aspartic acid, N-Sulfonic acid
2. L-Aspartic acid, 2β-sulfonic acid
3. L-Aspartic acid, 2β-sulfate
4. L-aspartic acid, 3α-sulfonic acid
5. L-aspartic acid, 3α-sulfate
6. L-aspartic acid, 3β-sulfonic acid
7. L-aspartic acid, 3β-sulfate
8. 2α,3-dicarboxy, propane-1-sulfonic acid
9. 2α,3-dicarboxy, propane-1-sulfate
10. 1α,2-carboxy ethane sulfonic acid
11. 1α,2-carboxy ethane sulfate
12. D-aspartic acid, N-sulfonic acid
13. 2β,3-carboxy, propane-1-sulfonic acid
14. 2β,3-carboxy, propane-1-sulfate
15. 1β,2-carboxy ethane-1-sulfonic acid
16. 1β,2-carboxy ethane-1-sulfate
17. D-aspartic acid, 2α-sulfonic acid
18. D-aspartic acid, 2α-sulfonic acid
19. D-Aspartic acid, 3α-sulfonic acid
20. D-Aspartic acid, 3α-sulfate
21. D-Aspartic acid, 3β-sulfonic acid
22. D-aspartic acid, 3β-sulfate
23. L-asparagine, N-sulfonic acid
24. 2α-carboxy, 3-carboxamido, propane-1-sulfonic acid
25. 2α-carboxy, 3-carboxamido, propane-1-sulfate
26. 1α-carboxy, 2-carboxamido, ethane sulfonic acid
27. 1α-carboxy, 2-carboxamido, ethane sulfate
28. L-asparagine, 2β-sulfonic acid
29. -asparagine, 2β-sulfate
30. L-asparagine, 3α-sulfonic acid
31. L-asparagine, 3α-sulfate
32. L-asparagine, 3β-sulfonic acid
33. L-asparagine, 3β-sulfate
34. D-asparagine, N-sulfonic acid
35. 2β-carboxy, 3-carboxamido, propane-1-sulfonic acid
36. 2β-carboxy, 3-carboxamido, propane-1-sulfate
37. 1β-carboxy, 2-carboxamido, ethane sulfonic acid]
38. 1β-carboxy, 2-carboxamido, ethane sulfate
39. D-asparagine, 2α-sulfonic acid
40. D-asparagine, 2α-sulfate
41. D-asparagine, 3α-sulfonic acid
42. D-asparagine, 3α-sulfate
43. D-asparagine, 3β-sulfonic acid
44. D-asparagine, 3β-sulfate
45. L-glutamic acid, N-sulfonic acid
46. 2α,4-dicarboxy, butane-1-sulfonic acid
47. 2α,4-dicarboxy, butane-1-sulfate
48. 1α,3-dicarboxy, propane sulfonic acid
49. 1α,3-dicarboxy, propane sulfate
50. 1β,3-dicarboxy, propane sulfate
51. 1β,3-dicarboxy, propane sulfonic acid
52. L-glutamic acid, 2β-sulfonic acid
53. L-glutamic acid, 2β-sulfate
54. L-glutamic acid, 3α-sulfonic acid
55. L-glutamic acid, 3α-sulfate
56. L-glutamic acid, 3β-sulfonic acid
57. L-glutamic acid, 3β-sulfate
58. L-glutamic acid, 4α-sulfonic acid
59. L-glutamic acid, 4α-sulfate
60. L-glutamic acid, 4β-sulfonic acid
61. L-glutamic acid, 4β-sulfate
62. D-glutamic acid, N-sulfonic acid
63. 2β,4-dicarboxy, butane-1-sulfonic acid
64. 2β,4-dicarboxy, butane-1-sulfate
65. D-glutamic acid, 2α-sulfonic acid
66. D-glutamic acid, 2α-sulfate
67. D-glutamic acid, 3α-sulfonic acid
68. D-glutamic acid, 3α-sulfate
69. D-glutamic acid, 3β-sulfonic acid
70. D-glutamic acid, 3β-sulfate
71. D-glutamic acid, 4α-sulfonic acid
72. D-glutamic acid, 4α-sulfate
73. D-glutamic acid, 4β-sulfonic acid
74. D-glutamic acid, 4β-sulfate
75. L-glutamine, N-sulfonic acid
76. L-glutamine, 2β-sulfonic acid
77. L-glutamine, 2β-sulfate
78. L-glutamine, 3α-sulfonic acid
79. L-glutamine, 3α-sulfate
80. L-glutamine, 3β-sulfonic acid
81. L-glutamine, 3β-sulfate
82. L-glutamine, 4α-sulfonic acid
83. L-glutamine, 4α-sulfate
84. L-glutamine, 4β-sulfonic acid
85. L-glutamine, 4β-sulfate
86. 2α-carboxy, 4-carboxamido, butane-1-sulfonic acid
87. 2α-carboxy, 4-carboxamido, butane-1-sulfate
88. 1α-carboxy, 3-carboxamido, propane-1-sulfonic acid
89. 1α-carboxy, 3-carboxamido, propane-1-sulfate
90. 1β-carboxy, 3-carboxamido, propane-1-sulfate
91. 1β-carboxy, 3-carboxamido, propane-1-sulfonic acid
92. D-glutamine, N-sulfonic acid
93. 2β-carboxy, 4-carboxamido, butane-1-sulfonic acid
94. 2β-carboxy, 4-carboxamido, butane-1-sulfate
95. D-glutamine, 2α-sulfonic acid
96. D-glutamine, 2α-sulfate
97. D-glutamine, 3α-sulfonic acid
98. D-glutamine, 3α-sulfate
99. D-glutamine, 3β-sulfonic acid 100. D-glutamine, 3β-sulfate
101. D-glutamine, 4α-sulfonic acid
102. D-glutamine, 4α-sulfate
103. D-glutamine, 4β-sulfonic acid
104. D-glutamine, 4β-sulfate
105. L-homoglutamic acid, N-sulfonic acid
106. Pentane-2α,5-dicarboxy-1-sulfonic acid
107. Pentane-2α,5-dicarboxy-1-sulfate
108. Butane-1α,4-dicarboxy-1-sulfonic acid
109. Butane-1α,4-dicarboxy-1-sulfate
110. L-homoglutamic acid, 2β-sulfonic acid
111. L-homoglutamic acid, 2β-sulfate
112. L-homoglutamic acid, 3α-sulfonic acid
113. L-homoglutamic acid, 3α-sulfate
114. L-homoglutamic acid, 3β-sulfonic acid
115. L-homoglutamic acid, 3β-sulfate
116. L-homoglutamic acid, 4α-sulfonic acid
117. L-homoglutamic acid, 4α-sulfate
118. L-homoglutamic acid, 4β-sulfonic acid
119. L-homoglutamic acid, 4β-sulfate
120. L-homoglutamic acid, 5α-sulfonic acid
121. L-homoglutamic acid, 5α-sulfate
122. L-homoglutamic acid, 5β-sulfonic acid
123. L-homoglutamic acid, 5β-sulfate
124. D-homoglutamic acid, N-sulfonic acid
125. Pentane-2β,5-dicarboxy-1-sulfonic acid
126. Pentane-2β,5-dicarboxy-1-sulfate
127. Butane-1β,4-dicarboxy-1-sulfonic acid
128. Butane-1β,4-dicarboxy-1-sulfate
129. D-homoglutamic acid, 2α-sulfonic acid
130. D-homoglutamic acid, 2α-sulfate
131. D-homoglutamic acid, 3α-sulfonic acid
132. D-homoglutamic acid, 3α-sulfate
133. D-homoglutamic acid, 3β-sulfonic acid
134. D-homoglutamic acid, 3β-sulfate
135. D-homoglutamic acid, 4α-sulfonic acid
136. D-homoglutamic acid, 4α-sulfate
137. D-homoglutamic acid, 4β-sulfonic acid
138. D-homoglutamic acid, 4β-sulfate
139. D-homoglutamic acid, 5α-sulfonic acid
140. D-homoglutamic acid, 5α-sulfate
141. D-homoglutamic acid, 5β-sulfonic acid
142. D-homoglutamic acid, 5β-sulfate
143. L-homoglutamine, N-sulfonic acid
144. Pentane-2α-carboxy, 5-carboxamido-1-sulfonic acid
145. Pentane-2α-carboxy, 5-carboxamido-1-sulfate
146. Butane-1α-carboxy, 4-carboxamido-1-sulfonic acid
147. Butane-1α-carboxy, 4-carboxamido-1-sulfate
148. L-homoglutamine, 2β-sulfonic acid
149. L-homoglutamine, 2β-sulfate
150. L-homoglutamine, 3α-sulfonic acid
151. L-homoglutamine, 3α-sulfate
152. L-homoglutamine, 3β-sulfonic acid
153. L-homoglutamine, 3β-sulfate
154. L-homoglutamine, 4α-sulfonic acid
155. L-homoglutamine, 4α-sulfate
156. L-homoglutamine, 4β-sulfonic acid
157. L-homoglutamine, 4β-sulfate
158. L-homoglutamine, 5α-sulfonic acid
159. L-homoglutamine, 5α-sulfate
160. L-homoglutamine, 5β-sulfonic acid
161. L-homoglutamine, 5β-sulfate
162. D-homoglutamine, N-sulfonic acid
163. Pentane-2β-carboxy, 5-carboxamido-1-sulfonic acid
164. Pentane-2β-carboxy, 5-carboxamido-1-sulfate
165. Butane-1β-carboxy, 4-carboxamido-1-sulfonic acid
166. Butane-1β-carboxy, 4-carboxamido-1-sulfate
167. D-homoglutamine, 2α-sulfonic acid
168. D-homoglutamine, 2α-sulfate
169. D-homoglutamine, 3α-sulfonic acid
170. D-homoglutamine, 3α-sulfate
171. D-homoglutamine, 3β-sulfonic acid
172. D-homoglutamine, 3β-sulfate
173. D-homoglutamine, 4α-sulfonic acid
174. D-homoglutamine, 4α-sulfate
175. D-homoglutamine, 4β-sulfonic acid
176. D-homoglutamine, 4β-sulfate
177. D-homoglutamine, 5α-sulfonic acid
178. D-homoglutamine, 5α-sulfate
179. D-homoglutamine, 5β-sulfonic acid
180. D-homoglutamine, 5β-sulfate.

e) a process for the preparation of sulfonic acid/sulfate derivatives of the formula (Ia) and non-toxic salts thereof:
1. A compound wherein Z=OH, $R_1$=NHSO$_3$H, $R_2$=$R_3$=$R_4$=H;
2. A compound wherein Z=OH, $R_1$=NH$_2$, $R_3$=$R_4$=H, $R_2$=SO$_3$H;
3. A compound in which Z=OH, $R_1$=NH$_2$, $R_3$=$R_4$=H, $R_2$=OSO$_3$H;
4. A compound in which Z=OH, $R_1$=NH$_2$, $R_2$=$R_4$=H, $R_3$=SO$_3$H;
5. A compound in which Z=OH, $R_1$=NH$_2$, $R_2$=$R_4$=H, $R_3$=OSO$_3$H;
6. A compound in which Z=OH, $R_1$=NH$_2$, $R_2$=$R_3$=H, $R_4$=SO$_3$H;
7. A compound in which Z=OH, $R_1$=NH$_2$, $R_2$=$R_3$=H, $R_4$=OSO$_3$H;
8. A compound in which Z=OH, $R_1$=$R_3$=$R_4$=H, $R_2$=CH$_2$SO$_3$H;
9. A compound in which Z=OH, $R_1$=$R_3$=$R_4$=H, $R_2$=CH$_2$OSO$_3$H;
10. A compound in which Z=OH, $R_1$=$R_3$=$R_4$=H, $R_2$=SO$_3$H;
11. A compound in which Z=OH, $R_1$=$R_3$=$R_4$=H, $R_2$=OSO$_3$H;
12. A compound in which Z=OH, $R_2$=NHSO$_3$H, $R_1$=$R_3$=$R_4$=H;
13. A compound in which Z=OH, $R_2$=H, $R_1$=CH$_2$SO$_3$H;
14. A compound in which Z=OH, $R_2$=H, $R_1$=CH$_2$OSO$_3$H;
15. A compound in which Z=OH, $R_2$=H, $R_1$=SO$_3$H;
16. A compound in which Z=OH, $R_2$=H, $R_1$=OSO$_3$H;
17. A compound in which Z=OH, $R_2$=NH$_2$, $R_3$=$R_4$=H, $R_1$=SO$_3$H;
18. A compound in which Z=OH, $R_2$=NH$_2$, $R_3$=$R_4$=H, $R_1$=SO$_3$H;
19. A compound in which Z=OH, $R_2$=NH$_2$, $R_1$=$R_4$=H, $R_3$=SO$_3$H;
20. A compound wherein Z=OH, $R_2$=NH$_2$, R=$R_4$=H, $R_3$=OSO$_3$H;
21. A compound wherein Z=OH, $R_2$=NH$_2$, $R_1$=$R_3$=H, $R_4$=SO$_3$H;
22. A compound wherein Z=OH, $R_2$=NH$_2$, $R_1$=$R_3$=H, $R_4$=OSO$_3$H;
23. A compound wherein $R_1$=NHSO$_3$H, $R_2$=$R_3$=$R_4$=H;
24. A compound wherein Z=NH$_2$, $R_1$=H, $R_2$=CH$_2$SO$_3$H;
25. A compound wherein Z=NH$_2$, $R_1$=H, $R_2$=CH$_2$OSO$_3$H;
26. A compound wherein Z=NH$_2$, $R_1$=H, $R_2$=SO$_3$H;
27. A compound wherein Z=NH$_2$, $R_1$=H, $R_2$=OSO$_3$H;
28. A compound wherein Z=$R_1$=NH$_2$, $R_2$=$R_4$=H, $R_2$=SO$_3$H;

29. A compound wherein Z=R$_1$=NH$_2$, R$_2$=R$_4$=H, R$_3$=OSO$_3$H;
30. A compound wherein Z=R$_1$=NH$_2$, R$_2$=R$_4$=H, R$_3$=SO$_3$H;
31. A compound wherein Z=R$_1$=NH$_2$, R$_2$=R$_4$=H, R$_3$=OSO$_3$H;
32. A compound wherein Z=R$_1$=NH$_2$, R$_2$=R$_3$=H, R$_4$=SO$_3$H;
33. A compound wherein Z=R$_1$=NH$_2$, R$_2$=R$_3$=H, R$_4$=OSO$_3$H;
34. A compound wherein Z=NH$_2$, R$_2$=NHSO$_3$H, R$_1$=R$_3$=R$_4$=H;
35. A compound wherein Z=NH$_2$, R$_2$ to R$_4$=H, R$_1$=CH$_2$SO$_3$H;
36. A compound wherein Z=NH$_2$, R$_2$ to R$_4$=H, R$_1$=CH$_2$SO$_3$H;
37. A compound wherein Z=OH, R$_2$ to R$_4$=H, R$_1$=SO$_3$H;
38. A compound wherein Z=OH, R$_2$ to R$_4$=H, R$_1$=OSO$_3$H;
39. A compound wherein Z=R$_2$=NH$_2$, R$_3$=R$_4$=H, R$_1$=SO$_3$H;
40. A compound wherein Z=R$_2$=NH$_2$, R$_3$=R$_4$=H, R$_1$=OSO$_3$H;
41. A compound wherein Z=R$_2$=NH$_2$, R$_1$=R$_4$=H, R$_3$=SO$_3$H;
42. A compound wherein Z=R$_2$=NH$_2$, R$_1$=R$_4$=H, R$_3$=OSO$_3$H;
43. A compound wherein Z=R$_2$=NH$_2$, R$_1$=R$_3$=H, R$_4$=SO$_3$H;
44. A compound wherein Z=R$_2$=NH$_2$, R$_1$=R$_3$=H, R$_4$=OSO$_3$H;

f) a process for the preparation of sulfonic acid/sulfate derivatives of the formula (Ib) and non-toxic salts thereof:
1. A compound wherein Z=OH, R$_1$=NHSO$_3$H, R$_2$=R$_3$=R$_4$=R$_5$=R$_6$=H;
2. A compound wherein Z=OH, R$_1$, R$_3$ to R$_6$=H, R$_2$=CH$_2$SO$_3$H;
3. A compound wherein Z=OH, R$_1$, R$_3$ to R$_6$=H, R$_2$=CH$_2$OSO$_3$H;
4. A compound wherein Z=OH, R$_1$, R$_3$ to R$_6$=H, R$_2$=SO$_3$H;
5. A compound wherein Z=OH, R$_1$, R$_3$ to R$_6$=H, R$_2$=OSO$_3$H;
6. A compound wherein Z=OH, R$_2$ to R$_6$=H, R$_1$=OSO$_3$H;
7. A compound wherein Z=OH, R$_2$ to R$_6$=H, R$_1$=SO$_3$H;
8. A compound wherein Z=OH, R$_1$=NH$_2$, R$_3$ to R$_6$=H, R$_2$=SO$_3$H;
9. A compound wherein Z=OH, R$_1$=NH$_2$, R$_3$ to R$_6$=H, R$_2$=OSO$_3$H;
10. A compound wherein Z=OH, R$_1$=NH$_2$, R$_2$=H, R$_4$ to R$_6$=H, R$_3$=SO$_3$H;
11. A compound wherein Z=OH, R$_1$=NH$_2$, R$_2$=H, R$_4$ to R$_6$=H, R$_3$=OSO$_3$H;
12. A compound wherein Z=OH, R$_1$=NH$_2$, R$_2$=R$_3$=R$_5$=R$_6$=H, R$_4$=SO$_3$H;
13. A compound wherein Z=OH, R$_1$=NH$_2$, R$_2$=R$_3$=R$_5$=R$_6$=H, R$_4$=OSO$_3$H;
14. A compound wherein Z=OH, R$_1$=NH$_2$, R$_2$=R$_3$=R$_4$=R$_6$=H, R$_5$=SO$_3$H;
15. A compound wherein Z=OH, R$_1$=NH$_2$, R$_2$=R$_3$=R$_4$=R$_6$=H, R$_5$=OSO$_3$H;
16. A compound wherein Z=OH, R$_1$=NH$_2$, R$_2$ to R$_5$=H, R$_6$=SO$_3$H;
17. A compound wherein Z=OH, R$_1$=NH$_2$, R$_2$ to R$_5$=H, R$_6$=OSO$_3$H;
18. A compound wherein Z=OH, R$_2$=NHSO$_3$H, R$_1$, R$_3$ to R$_6$=H;
19. A compound wherein Z=OH, R$_2$ to R$_6$=H, R$_1$=CH$_2$SO$_3$H;
20. A compound wherein Z=OH, R$_2$ to R$_6$=H, R$_1$=CH$_2$OSO$_3$H;
21. A compound wherein Z=OH, R$_2$=NH$_2$, R$_3$ to R$_6$H, R$_1$=SO$_3$H;
22. A compound wherein Z=OH, R$_2$=NH$_2$, R$_3$ to R$_6$H, R$_1$=OSO$_3$H;
23. A compound wherein Z=OH, R$_2$=NH$_2$, R$_1$, R$_4$ to R$_6$=H, R$_3$=SO$_3$H;
24. A compound wherein Z=OH, R$_2$=NH$_2$, R$_1$, R$_4$ to R$_6$=H, R$_3$=OSO$_3$H;
25. A compound wherein Z=OH, R$_2$=NH$_2$, R$_1$=R$_3$=R$_5$=R$_6$=H, R$_4$=SO$_3$H;
26. A compound wherein Z=OH, R$_2$=NH$_2$, R$_1$=R$_3$=R$_5$=R$_6$=H, R$_4$=OSO$_3$H;
27. A compound wherein Z=OH, R$_2$=NH$_2$, R$_1$=R$_3$=R$_4$=R$_6$=H, R$_5$=SO$_3$H;
28. A compound wherein Z=OH, R$_2$=NH$_2$, R$_1$=R$_3$=R$_4$=R$_6$=H, R$_5$=OSO$_3$H;
29. A compound wherein Z=OH, R$_2$=NH$_2$, R$_1$=R$_3$=R$_4$=R$_5$=H, &=SO$_3$H;
30. A compound wherein Z=OH, R$_2$=NH$_2$, R$_1$=R$_3$=R$_4$=R$_5$=H, R$_6$=OSO$_3$H;
31. A compound wherein Z=NH$_2$, R$_1$=NHSO$_3$H, R$_2$ to R$_6$=H;
32. A compound wherein Z=R$_1$=NH$_2$, R$_3$ to R$_6$=H, R$_2$=SO$_3$H;
33. A compound wherein Z=R$_1$=NH$_2$, R$_3$ to R$_6$=H, R$_2$=OSO$_3$H;
34. A compound wherein Z=R$_1$=NH$_2$, R$_2$=H, R$_3$ to R$_6$=H, R$_3$=SO$_3$H;
35. A compound wherein Z=R$_1$=NH$_2$, R$_2$=H, R$_3$ to R$_6$=H, R$_3$=OSO$_3$H;
36. A compound wherein Z=R$_1$=NH$_2$, R$_2$=R$_3$=R$_5$=R$_6$=H, R$_4$=SO$_3$H;
37. A compound wherein Z=R$_1$=NH$_2$, R$_2$=R$_3$=R$_5$=R$_6$=H, R$_4$=OSO$_3$H;
38. A compound wherein Z=R$_1$=NH$_2$, R$_2$=R$_3$=R$_4$=R$_6$=H, R$_5$=SO$_3$H;
39. A compound wherein Z=R$_1$=NH$_2$, R$_2$=R$_3$=R$_4$=R$_6$=H, R$_5$=OSO$_3$H;
40. A compound wherein Z=R$_1$=NH$_2$, R$_2$ to R$_5$=H, R$_6$=SO$_3$H;
41. A compound wherein Z=R$_1$=NH$_2$, R$_2$ to R$_5$=H, R$_6$=OSO$_3$H;
42. A compound wherein Z=NH$_2$, R$_1$, R$_3$ to R$_6$=H, R$_2$=CH$_2$SO$_3$H;
43. A compound wherein Z=NH$_2$, R$_1$, R$_3$ to R$_6$=H, R$_2$=CH$_2$OSO$_3$H;
44. A compound wherein Z=NH$_2$, R$_1$, R$_3$ to R$_6$=H, R$_2$=SO$_3$H;
45. A compound wherein Z=NH$_2$, R$_1$, R$_3$ to R$_6$=H, R$_2$=OSO$_3$H;
46. A compound wherein Z=NH$_2$, R$_2$ to R$_6$=H, R$_1$=OSO$_3$H;
47. A compound wherein Z=NH$_2$, R$_2$ to R$_6$=H, R$_1$=SO$_3$H;
48. A compound wherein Z=NH$_2$, R$_2$=NHSO$_3$H; R$_1$=H, R$_3$ to R$_6$=H;
49. A compound wherein Z=NH$_2$, R$_2$ to R$_6$=H, R$_1$=CH$_2$SO$_3$H;
50. A compound wherein Z=NH$_2$, R$_2$ to R$_6$=H, R$_1$=CH$_2$OSO$_3$H;

51. A compound wherein Z=NH$_2$, R$_2$=NH$_2$, R$_3$ to R$_6$=H, R$_1$=SO$_3$H;
52. A compound wherein Z=NH$_2$, R$_2$=NH$_2$, R$_3$ to R$_6$=H, R$_1$=OSO$_3$H;
53. A compound wherein Z=NH$_2$, R$_2$=NH$_2$, R$_1$, R$_4$ to R$_6$H, R$_3$=SO$_3$H;
54. A compound wherein Z=R$_2$=NH$_2$, R$_1$, R$_4$ to R$_6$H, R$_3$=OSO$_3$H;
55. A compound wherein Z=R$_2$=NH$_2$, R$_1$=R$_3$=R$_5$=R$_6$=H, R$_4$=SO$_3$H;
56. A compound wherein Z=R$_2$=NH$_2$, R$_1$=R$_3$=R$_5$=R$_6$=H, R$_4$=OSO$_3$H;
57. A compound wherein Z=R$_2$=NH$_2$, R$_1$=R$_3$=P4=R$_6$=H, R$_5$=SO$_3$H;
58. A compound wherein Z=R$_2$=NH$_2$, R$_1$=R$_3$=R$_4$=R$_6$=H, R$_5$=OSO$_3$H;
59. A compound wherein Z=R$_2$=NH$_2$, R$_1$=R$_3$=R$_4$=R$_5$=H, R$_6$=SO$_3$H;
60. A compound wherein Z=R$_2$=NH$_2$, R$_1$=R$_3$=R$_4$=R$_5$=H, R$_6$=OSO$_3$H;

g) a process for the preparation of sulfonic acid/sulfate derivatives of the formula (Ic) and non-toxic salts thereof:
1. A compound wherein Z=OH, R$_1$=NHSO$_3$H, R$_2$ to R$_8$=H;
2. A compound wherein Z=OH, R$_1$, R$_3$ to R$_8$=H, R$_2$=CH$_2$SO$_3$H;
3. A compound wherein Z=OH, R$_1$, R$_3$ to R$_8$=H, R$_2$=CH$_2$OSO$_3$H;
4. A compound wherein Z=OH, R$_1$, R$_3$ to R$_8$=H, R$_2$=SO$_3$H;
5. A compound wherein Z=OH, R$_1$, R$_3$ to R$_8$=H, R$_2$=OSO$_3$H;
6. A compound wherein Z=OH, R$_1$=NH$_2$, R$_3$ to R$_8$=H, R$_2$=SO$_3$H;
7. A compound wherein Z=OH, R$_1$=NH$_2$, R$_3$ to R$_8$=H, R$_2$=OSO$_3$1H;
8. A compound wherein Z=OH, R$_1$=NH$_2$, R$_2$=H, R$_4$ to R$_8$=H, R$_3$=SO$_3$H;
9. A compound wherein Z=OH, R$_1$=NH$_2$, R$_2$=H, R$_4$ to R$_8$=H, R$_3$=OSO$_3$H;
10. A compound wherein Z=OH, R$_1$=NH$_2$, R$_2$=R$_3$=H, R$_5$ to R$_8$=H, R$_4$=SO$_3$H;
11. A compound wherein Z=OH, R$_1$=NH$_2$, R$_2$=R$_3$=H, R$_5$ to R$_8$=H, R$_4$=OSO$_3$H;
12. A compound wherein Z=OH, R$_1$=NH$_2$, R$_2$=R$_3$=R$_4$=H, R$_6$ to R$_8$=H, R$_5$=SO$_3$H;
13. A compound wherein Z=OH, R$_1$=NH$_2$, R$_2$=R$_3$=R$_4$=H, R$_6$ to R$_8$=H, R$_5$=OSO$_3$H;
14. A compound wherein Z=OH, R$_1$=NH$_2$, R$_2$=R$_5$=H, R$_7$=R$_8$=H, R$_6$=SO$_3$H;
15. A compound wherein Z=OH, R$_1$=NH$_2$, R$_2$=R$_5$=H, R$_7$=R$_8$=H, R$_6$=OSO$_3$H;
16. A compound wherein Z=OH, R$_1$=NH$_2$, R$_2$ to R$_6$=H, R$_8$=H, R$_7$=SO$_3$H
17. A compound wherein Z=OH, R$_1$=NH$_2$, R$_2$ to R$_6$=H, R$_8$=H, R$_7$=OSO$_3$H;
18. A compound wherein Z=OH, R$_1$=NH$_2$, R$_2$ to R$_7$=H, R$_8$=SO$_3$H;
19. A compound wherein Z=OH, R$_1$=NH$_2$, R$_2$ to R$_7$=H, R$_8$=OSO$_3$H;
20. A compound wherein Z=OH, R$_2$=NHSO$_3$H, R$_1$, R$_3$ to R$_8$=H;
21. A compound wherein Z=OH, R$_2$ to R$_8$=H, R$_1$=CH$_2$SO$_3$H;
22. A compound wherein Z=OH, R$_2$ to R$_8$=H, R$_1$=CH$_2$OSO$_3$H;
23. A compound wherein Z=OH, R$_2$ to R$_8$=H, R$_1$=SO$_3$H;
24. A compound wherein Z=OH, R$_2$ to R$_8$=H, R$_1$=OSO$_3$H;
25. A compound wherein Z=OH, R$_2$=NH$_2$, R$_3$ to R$_8$=H, R$_1$=SO$_3$H;
26. A compound wherein Z=OH, R$_2$=NH$_2$, R$_3$ to R$_8$=H, R$_1$=OSO$_3$H;
27. A compound wherein Z=OH, R$_2$=NH$_2$, R$_1$, R$_4$ to R$_8$=H, R$_3$=SO$_3$H;
28. A compound wherein Z=OH, R$_2$=NH$_2$, R$_1$, R$_4$ to R$_8$=H, R$_3$=OSO$_3$H;
29. A compound wherein Z=OH, R$_2$=NH$_2$, R$_1$=R$_3$=H, R$_5$ to R$_8$=H, R$_4$=SO$_3$H;
30. A compound wherein Z=OH, R$_2$=NH$_2$, R$_1$=R$_3$=H, R$_5$ to R$_8$=H, R$_4$=OSO$_3$H;
31. A compound wherein Z=OH, R$_2$=NH$_2$, R$_1$=R$_3$=R$_4$=H, R$_6$ to R$_8$=H, R$_5$=SO$_3$H;
32. A compound wherein Z=OH, R$_2$=NH$_2$, R$_1$=R$_3$=R$_4$=H, R$_6$ to R$_8$=H, R$_5$=OSO$_3$H;
33. A compound wherein Z=OH, R$_2$=NH$_2$, R$_1$=H, R$_3$ to R$_5$=H, R$_7$=R$_8$=H, R$_6$=SO$_3$H;
34. A compound wherein Z=OH, R$_2$=NH$_2$, R$_1$=H, R$_3$ to R$_5$=H, R$_7$=R$_8$=H, R$_6$=OSO$_3$H;
35. A compound wherein Z=OH, R$_2$=NH$_2$, R=R$_8$=H, R$_3$ to R$_6$=H, R$_7$=SO$_3$H;
36. A compound wherein Z=OH, R$_2$=NH$_2$, R$_1$=R$_8$=H, R$_3$ to R$_6$=H, R$_7$=OSO$_3$H;
37. A compound wherein Z=OH, R$_2$=NH$_2$, R$_1$=H, R$_3$ to R$_7$=H, R$_8$=SO$_3$H;
38. A compound wherein Z=OH, R$_2$=NH$_2$, R$_1$=H, R$_3$ to R$_7$=H, R$_8$=OSO$_3$H;
39. A compound wherein Z=NH$_2$, R$_1$=NHSO$_3$H, R$_2$ to R$_8$=H;
40. A compound wherein Z=NH$_2$, R$_1$ and R$_3$ to R$_8$=H, R$_2$=CH$_2$SO$_3$H;
41. A compound wherein Z=NH$_2$, R$_1$ and R$_3$ to R$_8$=H, R$_2$=CH$_2$OSO$_3$H;
42. A compound wherein Z=NH$_2$, R$_1$ and R$_3$ to R$_8$=H, R$_2$=SO$_3$H;
43. A compound wherein Z=NH$_2$, R$_1$ and R$_3$ to R$_8$=H, R$_2$=OSO$_3$H;
44. A compound wherein Z=R$_1$=NH$_2$, R$_3$ to R$_8$=H, R$_2$=SO$_3$H;
45. A compound wherein Z=R$_1$=NH$_2$, R$_3$ to R$_8$=H, R$_2$=OSO$_3$H;
46. A compound wherein Z=R$_1$=NH$_2$, R$_2$=H, R$_4$ to R$_8$=H, R$_3$=SO$_3$H;
47. A compound wherein Z=R$_1$=NH$_2$, R$_2$=H, R$_4$ to R$_8$=H, R$_3$=OSO$_3$H;
48. A compound wherein Z=R$_1$=NH$_2$, R$_2$=R$_3$=H, R$_5$ to R$_8$=H, R$_4$=SO$_3$H;
49. A compound wherein Z=R$_1$=NH$_2$, R$_2$=R$_3$=H, R$_5$ to R$_8$=H, R$_4$=OSO$_3$H;
50. A compound wherein Z=R$_1$=NH$_2$, R$_2$=R$_3$=R$_4$=H, R$_6$ to R$_8$=H, R$_5$=SO$_3$H;

51. A compound wherein Z=R$_1$=NH$_2$, R$_2$=R$_3$=R$_4$=H, R$_6$ to R$_8$=H, R$_5$=OSO$_3$H;
52. A compound wherein Z=R$_1$=NH$_2$, R$_2$=R$_5$=H, R$_7$=R$_8$=H, R$_6$=SO$_3$H;
53. A compound wherein Z=R$_1$=NH$_2$, R$_2$=R$_5$=H, R$_7$=R$_8$=H, R$_6$=OSO$_3$H;
54. A compound wherein Z=R$_1$=NH$_2$, R$_2$ to R$_6$=H, R$_8$=H, R$_7$=SO$_3$H;
55. A compound wherein Z=R$_1$=NH$_2$, R$_2$ to R$_6$=H, R$_8$=H, R$_7$=OSO$_3$H;
56. A compound wherein Z=R$_1$=NH$_2$, R$_2$ to R$_7$=H, R$_8$=SO$_3$H;
57. A compound wherein Z=R$_1$=NH$_2$, R$_2$ to R$_7$=H, R$_8$=OSO$_3$H;
58. A compound wherein Z=NH$_2$, R$_2$=NHSO$_3$H, R$_1$ and R$_3$ to R$_8$=H;
59. A compound wherein Z=NH$_2$, R$_2$ to R$_8$=H, R$_1$=CH$_2$SO$_3$H;
60. A compound wherein Z=NH$_2$, R$_2$ to R$_8$=H, R$_1$=CH$_2$OSO$_3$H;
61. A compound wherein Z=NH$_2$, R$_2$ to R$_8$=H, R$_1$=SO$_3$H;
62. A compound wherein Z=NH$_2$, R$_2$ to R$_8$=H, R$_1$=OSO$_3$H;
63. A compound wherein Z=R$_2$=NH$_2$, R$_3$ to R$_8$=H, R$_1$=SO$_3$H;
64. A compound wherein Z=R$_2$=NH$_2$, R$_3$ to R$_8$=H, R$_1$=OSO$_3$H;
65. A compound wherein Z=R$_2$=NH$_2$, R$_1$, R$_4$ to R$_8$=H, R$_3$=SO$_3$H;
66. A compound wherein Z=R$_2$=NH$_2$, R$_1$, R$_4$ to R$_8$=H, R$_3$=OSO$_3$H;
67. A compound wherein Z=R$_2$=NH$_2$, R$_1$=R$_3$=H, R$_5$ to R$_8$=H, R$_4$=SO$_3$H;
68. A compound wherein Z=R$_2$=NH$_2$, R$_1$=R$_3$=H, R$_5$ to R$_8$=H, R$_4$=OSO$_3$H;
69. A compound wherein Z=R$_2$=NH$_2$, R$_1$=R$_3$=R$_4$=H, R$_6$ to R$_8$=H, R$_5$=SO$_3$H;
70. A compound wherein Z=R$_2$=NH$_2$, R$_1$=R$_3$=R$_4$=H, R$_6$ to R$_8$=H, R$_5$=OSO$_3$H;
71. A compound wherein Z=R$_2$=NH$_2$, R$_1$=H, R$_3$ to R$_5$=H, R$_7$=R$_8$=H, R$_6$=SO$_3$H;
72. A compound wherein Z=R$_2$=NH$_2$, R$_1$=H, R$_3$ to R$_5$=H, R$_7$=R$_8$=H, R$_6$=OSO$_3$H;
73. A compound wherein Z=R$_2$=NH$_2$, R$_1$=R$_8$=H, R$_3$ to R$_6$=H, R$_7$=SO$_3$H;
74. A compound wherein Z=R$_2$=NH$_2$, R$_1$=R$_8$=H, R$_3$ to R$_6$=H, R$_7$=OSO$_3$H;
75. A compound wherein Z=R$_2$=NH$_2$, R$_1$=H, R$_3$ to R$_7$=H, R$_8$=SO$_3$H;
76. A compound wherein Z=R$_2$=NH$_2$, R$_1$=H, R$_3$ to R$_7$=H, R$_8$=OSO$_3$H.

h) In the compound of the present invention of the formula (Ia) wherein the compound is selected from the group consisting of aspartic acid, asparagine and corresponding de-amino analogs:
1. L-Aspartic acid, N-Sulfonic acid
2. L-Aspartic acid, 2β-sulfonic acid
3. L-Aspartic acid, 2β-sulfate
4. L-aspartic acid, 3α-sulfonic acid
5. L-aspartic acid, 3α-sulfate
6. L-aspartic acid, 3β-sulfonic acid
7. L-aspartic acid, 3β-sulfate
8. 2α,3-dicarboxy, propane-1-sulfonic acid
9. 2α,3-dicarboxy, propane-1-sulfate
10. 1α,2-carboxy ethane sulfonic acid
11. 1α,2-carboxy ethane sulfate
12. D-aspartic acid, N-sulfonic acid
13. 2β,3-carboxy, propane-1-sulfonic acid
14. 2β,3-carboxy, propane-1-sulfate
15. 1β,2-carboxy ethane-1-sulfonic acid
16. 1β,2-carboxy ethane-1-sulfate
17. D-aspartic acid, 2α-sulfonic acid
18. D-aspartic acid, 2α-sulfonic acid
19. D-Aspartic acid, 3α-sulfonic acid
20. D-Aspartic acid, 3α-sulfate
21. D-Aspartic acid, 3β-sulfonic acid
22. D-aspartic acid, 3β-sulfate
23. L-asparagine, N-sulfonic acid
24. 2α-carboxy, 3-carboxamido, propane-1-sulfonic acid
25. 2α-carboxy, 3-carboxamido, propane-1-sulfate
26. 1α-carboxy, 2-carboxamido, ethane sulfonic acid
27. 1α-carboxy, 2-carboxamido, ethane sulfate
28. L-asparagine, 2β-sulfonic acid
29. -asparagine, 2β-sulfate
30. L-asparagine, 3α-sulfonic acid
31. L-asparagine, 3α-sulfate
32. L-asparagine, 3β-sulfonic acid
33. L-asparagine, 3β-sulfate
34. D-asparagine, N-sulfonic acid
35. 2β-carboxy, 3-carboxamido, propane-1-sulfonic acid
36. 2β-carboxy, 3-carboxamido, propane-1-sulfate
37. 1β-carboxy, 2-carboxamido, ethane sulfonic acid]
38. 1β-carboxy, 2-carboxamido, ethane sulfate
39. D-asparagine, 2α-sulfonic acid
40. D-asparagine, 2α-sulfate
41. D-asparagine, 3α-sulfonic acid
42. D-asparagine, 3α-sulfate
43. D-asparagine, 3β-sulfonic acid
44. D-asparagine, 3β-sulfate.

i) In the compound of the present invention of the formula (Ib) wherein the compound is selected from the group consisting of glutamic acid, glutamine and corresponding de-amino analogs:
1. 1 L-glutamic acid, N-sulfonic acid
2. 2α,4-dicarboxy, butane-1-sulfonic acid
3. 2α,4-dicarboxy, butane-1-sulfate
4. 1α,3-dicarboxy, propane sulfonic acid
5. 1α,3-dicarboxy, propane sulfate
6. 1β,3-dicarboxy, propane sulfate
7. 1β,3-dicarboxy, propane sulfonic acid
8. L-glutamic acid, 2β-sulfonic acid
9. L-glutamic acid, 2β-sulfate
10. L-glutamic acid, 3α-sulfonic acid
11. L-glutamic acid, 3α-sulfate
12. L-glutamic acid, 3β-sulfonic acid
13. L-glutamic acid, 3β-sulfate
14. L-glutamic acid, 4α-sulfonic acid
15. L-glutamic acid, 4α-sulfate
16. L-glutamic acid, 4β-sulfonic acid
17. L-glutamic acid, 4β-sulfate
18. D-glutamic acid, N-sulfonic acid
19. 2β,4-dicarboxy, butane-1-sulfonic acid
20. 2β,4-dicarboxy, butane-1-sulfate
21. D-glutamic acid, 2α-sulfonic acid
22. D-glutamic acid, 2α-sulfate
23. D-glutamic acid, 3α-sulfonic acid
24. D-glutamic acid, 3α-sulfate
25. D-glutamic acid, 3β-sulfonic acid
26. D-glutamic acid, 3β-sulfate 27. D-glutamic acid, 4α-sulfonic acid
28. D-glutamic acid, 4α-sulfate
29. D-glutamic acid, 4β-sulfonic acid
30. D-glutamic acid, 4β-sulfate
31. L-glutamine, N-sulfonic acid
32. L-glutamine, 2β-sulfonic acid
33. L-glutamine, 2β-sulfate
34. L-glutamine, 3α-sulfonic acid
35. L-glutamine, 3α-sulfate
36. L-glutamine, 3β-sulfonic acid
37. L-glutamine, 3β-sulfate
38. L-glutamine, 4α-sulfonic acid
39. L-glutamine, 4α-sulfate
40. L-glutamine, 4β-sulfonic acid
41. L-glutamine, 4β-sulfate
42. 2α-carboxy, 4-carboxamido, butane-1-sulfonic acid
43. 2α-carboxy, 4-carboxamido, butane-1-sulfate
44. 1α-carboxy, 3-carboxamido, propane-1-sulfonic acid
45. 1α-carboxy, 3-carboxamido, propane-1-sulfate
46. 1β-carboxy, 3-carboxamido, propane-1-sulfate
47. 1β-carboxy, 3-carboxamido, propane-1-sulfonic acid
48. D-glutamine, N-sulfonic acid
49. 2β-carboxy, 4-carboxamido, butane-1-sulfonic acid
50. 2β-carboxy, 4-carboxamido, butane-1-sulfate
51. D-glutamine, 2α-sulfonic acid
52. D-glutamine, 2α-sulfate
53. D-glutamine, 3α-sulfonic acid
54. D-glutamine, 3α-sulfate
55. D-glutamine, 3β-sulfonic acid
56. D-glutamine, 3β-sulfate
57. D-glutamine, 4α-sulfonic acid
58. D-glutamine, 4α-sulfate
59. D-glutamine, 4β-sulfonic acid
60. D-glutamine, 4β-sulfate j) In the compound of the present invention of the formula (Ic) wherein the compound is selected from the group consisting of homoglutamic acid, homoglutamine and corresponding de-amino analogs:
1. L-homoglutamic acid, N-sulfonic acid
2. Pentane-2α,5-dicarboxy-1-sulfonic acid
3. Pentane-2α,5-dicarboxy-1-sulfate
4. Butane-1α,4-dicarboxy-1-sulfonic acid
5. Butane-1α,4-dicarboxy-1-sulfate
6. L-homoglutamic acid, 2β-sulfonic acid
7. L-homoglutamic acid, 2β-sulfate
8. L-homoglutamic acid, 3α-sulfonic acid
9. L-homoglutamic acid, 3α-sulfate
10. L-homoglutamic acid, 3β-sulfonic acid
11. L-homoglutamic acid, 3β-sulfate
12. L-homoglutamic acid, 4α-sulfonic acid
13. L-homoglutamic acid, 4α-sulfate
14. L-homoglutamic acid, 4β-sulfonic acid
15. L-homoglutamic acid, 4β-sulfate
16. L-homoglutamic acid, 5α-sulfonic acid
17. L-homoglutamic acid, 5α-sulfate
18. L-homoglutamic acid, 5β-sulfonic acid
19. L-homoglutamic acid, 5β-sulfate
20. D-homoglutamic acid, N-sulfonic acid
21. Pentane-2β,5-dicarboxy-1-sulfonic acid
22. Pentane-2β,5-dicarboxy-1-sulfate
23. Butane-1β,4-dicarboxy-1-sulfonic acid
24. Butane-1β,4-dicarboxy-1-sulfate
25. D-homoglutamic acid, 2α-sulfonic acid
26. D-homoglutamic acid, 2α-sulfate
27. D-homoglutamic acid, 3α-sulfonic acid
28. D-homoglutamic acid, 3α-sulfate
29. D-homoglutamic acid, 3β-sulfonic acid
30. D-homoglutamic acid, 3β-sulfate
31. D-homoglutamic acid, 4α-sulfonic acid
32. D-homoglutamic acid, 4α-sulfate
33. D-homoglutamic acid, 4β-sulfonic acid
34. D-homoglutamic acid, 4β-sulfate
35. D-homoglutamic acid, 5α-sulfonic acid
36. D-homoglutamic acid, 5α-sulfate
37. D-homoglutamic acid, 5β-sulfonic acid
38. D-homoglutamic acid, 5β-sulfate
39. L-homoglutamine, N-sulfonic acid
40. Pentane-2α-carboxy, 5-carboxamido-1-sulfonic acid
41. Pentane-2α-carboxy, 5-carboxamido-1-sulfate
42. Butane-1α-carboxy, 4-carboxamido-1-sulfonic acid
43. Butane-1α-carboxy, 4-carboxamido-1-sulfate
44. L-homoglutamine, 2β-sulfonic acid
45. L-homoglutamine, 2β-sulfate
46. L-homoglutamine, 3α-sulfonic acid
47. L-homoglutamine, 3α-sulfate
48. L-homoglutamine, 3β-sulfonic acid
49. L-homoglutamine, 3β-sulfate
50. L-homoglutamine, 4α-sulfonic acid
51. L-homoglutamine, 4α-sulfate
52. L-homoglutamine, 4β-sulfonic acid
53. L-homoglutamine, 4β-sulfate
54. L-homoglutamine, 5α-sulfonic acid
55. L-homoglutamine, 5α-sulfate
56. L-homoglutamine, 5β-sulfonic acid
57. L-homoglutamine, 5β-sulfate
58. D-homoglutamine, N-sulfonic acid
59. Pentane-2β-carboxy, 5-carboxamido-1-sulfonic acid
60. Pentane-2β-carboxy, 5-carboxamido-1-sulfate
61. Butane-1β-carboxy, 4-carboxamido-1-sulfonic acid
62. Butane-1β-carboxy, 4-carboxamido-1-sulfate
63. D-homoglutamine, 2α-sulfonic acid
64. D-homoglutamine, 2α-sulfate
65. D-homoglutamine, 3α-sulfonic acid
66. D-homoglutamine, 3α-sulfate
67. D-homoglutamine, 3β-sulfonic acid
68. D-homoglutamine, 3β-sulfate
69. D-homoglutamine, 4α-sulfonic acid
70. D-homoglutamine, 4α-sulfate
71. D-homoglutamine, 4β-sulfonic acid
72. D-homoglutamine, 4β-sulfate
73. D-homoglutamine, 5α-sulfonic acid
74. D-homoglutamine, 5α-sulfate
75. D-homoglutamine, 5β-sulfonic acid
76. D-homoglutamine, 5β-sulfate The preferable specific compounds of the formulae (Ia), (Ib) and (Ic) are the derivatives of aspartic acid, asparagine and corresponding de-amino analogs (Table 1), glutamic acid, glutamine and corresponding de-amino analogs (Table 2) and homoglutamic acid, homoglutamine and corresponding de-amino analogs (Table 3) and non toxic salts thereof and example compounds.

TABLE 1

Structure 1

| # | Compound | Substituents |
|---|---|---|
| 1. | L-Aspartic acid, N-Sulfonic acid | $Z = OH, R_1 = NHSO_3H, R_2 = R_3 = R_4 = H$ |
| 2. | L-Aspartic acid, 2β-sulfonic acid | $Z = OH, R_1 = NH_2, R_3 = R_4 = H, R_2 = SO_3H$ |
| 3. | L-Aspartic acid, 2β-sulfate | $Z = OH, R_1 = NH_2, R_3 = R_4 = H, R_2 = OSO_3H$ |
| 4. | L-aspartic acid, 3α-sulfonic acid | $Z = OH, R_1 = NH_2, R_2 = R_4 = H, R_3 = SO_3H$ |
| 5. | L-aspartic acid, 3α-sulfate | $Z = OH, R_1 = NH_2, R_2 = R_4 = H, R_3 = OSO_3H$ |
| 6. | L-aspartic acid, 3β-sulfonic acid | $Z = OH, R_1 = NH_2, R_2 = R_3 = H, R_4 = SO_3H$ |
| 7. | L-aspartic acid, 3β-sulfate | $Z = OH, R_1 = NH_2, R_2 = R_3 = H, R_4 = OSO_3H$ |
| 8. | 2α, 3-dicarboxy, propane-1-sulfonic acid | $Z = OH, R_1 = R_3 = R_4 = H, R_2 = CH_2SO_3H$ |
| 9. | 2α, 3-dicarboxy, propane-1-sulfate | $Z = OH, R_1 = R_3 = R_4 = H, R_2 = CH_2OSO_3H$ |
| 10. | 1α, 2-carboxy ethane sulfonic acid | $Z = OH, R_1 = R_3 = R_4 = H, R_2 = SO_3H$ |
| 11. | 1α, 2-carboxy ethane sulfate | $Z = OH, R_1 = R_3 = R_4 = H, R_2 = OSO_3H$ |
| 12. | D-aspartic acid, N-sulfonic acid | $Z = OH, R_2 = NHSO_3H, R_1 = R_3 = R_4 = H$ |
| 13. | 2β, 3-carboxy, propane-1-sulfonic acid | $Z = OH, R_2 = H, R_1 = CH_2SO_3H$ |
| 14. | 2β, 3-carboxy, propane-1-sulfate | $Z = OH, R_2 = H, R_1 = CH_2OSO_3H$ |
| 15. | 1β, 2-carboxy ethane-1-sulfonic acid | $Z = OH, R_2 = H, R_1 = SO_3H$ |
| 16. | 1β, 2-carboxy ethane-1-sulfate | $Z = OH, R_2 = H, R_1 = OSO_3H$ |
| 17. | D-aspartic acid, 2α-sulfonic acid | $Z = OH, R_2 = NH_2, R_3 = R_4 = H, R_1 = SO_3H$ |
| 18. | D-aspartic acid, 2α-sulfonic acid | $Z = OH, R_2 = NH_2, R_3 = R_4 = H, R_1 = SO_3H$ |
| 19. | D-Aspartic acid, 3α-sulfonic acid | $Z = OH, R_2 = NH_2, R_1 = R_4 = H, R_3 = SO_3H$ |
| 20. | D-Aspartic acid, 3α-sulfate | $Z = OH, R_2 = NH_2, R_1 = R_4 = H, R_3 = OSO_3H$ |
| 21. | D-Aspartic acid, 3β-sulfonic acid | $Z = OH, R_2 = NH_2, R_1 = R_3 = H, R_4 = SO_3H$ |
| 22. | D-aspartic acid, 3β-sulfate | $Z = OH, R_2 = NH_2, R_1 = R_3 = H, R_4 = OSO_3H$ |
| 23. | L-asparagine, N-sulfonic acid | $Z = NH_2, R_1 = NHSO_3H, R_2 = R_3 = R_4 = H$ |
| 24. | 2α-carboxy, 3-carboxamido, propane-1-sulfonic acid | $Z = NH_2, R_1 = H, R_2 = CH_2SO_3H$ |
| 25. | 2α-carboxy, 3-carboxamido, propane-1-sulfate | $Z = NH_2, R_1 = H, R_2 = CH_2OSO_3H$ |
| 26. | 1α-carboxy, 2-carboxamido, ethane sulfonic acid | $Z = NH_2, R_1 = H, R_2 = SO_3H$ |
| 27. | 1α-carboxy, 2-carboxamido, ethane sulfate | $Z = NH_2, R_1 = H, R_2 = OSO_3H$ |
| 28. | L-asparagine, 2β-sulfonic acid | $Z = R_1 = NH_2, R_3 = R_4 = H, R_2 = SO_3H$ |
| 29. | L-asparagine, 2β-sulfate | $Z = R_1 = NH_2, R_2 = R_4 = H, R_3 = OSO_3H$ |
| 30. | L-asparagine, 3α-sulfonic acid | $Z = R_1 = NH_2, R_2 = R_4 = H, R_3 = SO_3H$ |
| 31. | L-asparagine, 3α-sulfate | $Z = R_1 = NH_2, R_2 = R_4 = H, R_3 = OSO_3H$ |
| 32. | L-asparagine, 3β-sulfonic acid | $Z = R_1 = NH_2, R_2 = R_3 = H, R_4 = SO_3H$ |
| 33. | L-asparagine, 3β-sulfate | $Z = R_1 = NH_2, R_2 = R_3 = H, R_4 = OSO_3H$ |
| 34. | D-asparagine, N-sulfonic acid | $Z = NH_2, R_2 = NHSO_3H, R_1 = R_3 = R_4 = H$ |
| 35. | 2β-carboxy, 3-carboxamido, propane-1-sulfonic acid | $Z = NH_2, R_2$ to $R_4 = H, R_1 = CH_2SO_3H$ |
| 36. | 2β-carboxy, 3-carboxamido, propane-1-sulfate | $Z = NH_2, R_2$ to $R_4 = H, R_1 = CH_2SO_3H$ |
| 37. | 1β-carboxy, 2-carboxamido, ethane sulfonic acid] | $Z = OH, R_2$ to $R_4 = H, R_1 = SO_3H$ |
| 38. | 1β-carboxy, 2-carboxamido, ethane sulfate | $Z = OH, R_2$ to $R_4 = H, R_1 = OSO_3H$ |
| 39. | D-asparagine, 2α-sulfonic acid | $Z = R_2 = NH_2, R_3 = R_4 = H, R_1 = SO_3H$ |
| 40. | D-asparagine, 2α-sulfate | $Z = R_2 = NH_2, R_3 = R_4 = H, R_1 = OSO_3H$ |
| 41. | D-asparagine, 3α-sulfonic acid | $Z = R_2 = NH_2, R_1 = R_4 = H, R_3 = SO_3H$ |
| 42. | D-asparagine, 3α-sulfate | $Z = R_2 = NH_2, R_1 = R_4 = H, R_3 = OSO_3H$ |
| 43. | D-asparagine, 3β-sulfonic acid | $Z = R_2 = NH_2, R_1 = R_3 = H, R_4 = SO_3H$ |
| 44. | D-asparagine, 3β-sulfate | $Z = R_2 = NH_2, R_1 = R_3 = H, R_4 = OSO_3H$ |

TABLE 2

Structure 2

| # | Compound | Substituents |
|---|---|---|
| 1. | L-glutamic acid, N-sulfonic acid | $Z = OH, R_1 = NHSO_3H, R_2 = R_3 = R_4 = R_5 = R_6 = H$ |
| 2. | 2α, 4-dicarboxy, butane-1-sulfonic acid | $Z = OH, R_1, R_3$ to $R_6 = H, R_2 = CH_2SO_3H$ |
| 3. | 2α, 4-dicarboxy, butane-1-sulfate | $Z = OH, R_1, R_3$ to $R_6 = H, R_2 = CH_2OSO_3H$ |
| 4. | 1α, 3-dicarboxy, propane sulfonic acid | $Z = OH, R_1, R_3$ to $R_6 = H, R_2 = SO_3H$ |
| 5. | 1α, 3-dicarboxy, propane sulfate | $Z = OH, R_1, R_3$ to $R_6 = H, R_2 = OSO_3H$ |
| 6. | 1β, 3-dicarboxy, propane sulfate | $Z = OH, R_2$ to $R_6 = H, R_1 = OSO_3H$ |
| 7. | 1β, 3-dicarboxy, propane sulfonic acid | $Z = OH, R_2$ to $R_6 = H, R_1 = SO_3H$ |
| 8. | L-glutamic acid, 2β-sulfonic acid | $Z = OH, R_1 = NH_2, R_3$ to $R_6 = H, R_2 = SO_3H$ |
| 9. | L-glutamic acid, 2β-sulfate | $Z = OH, R_1 = NH_2, R_3$ to $R_6 = H, R_2 = OSO_3H$ |
| 10. | L-glutamic acid, 3α-sulfonic acid | $Z = OH, R_1 = NH_2, R_2 = H, R_4$ to $R_6 = H, R_3 = SO_3H$ |
| 11. | L-glutamic acid, 3α-sulfate | $Z = OH, R_1 = NH_2, R_2 = H, R_4$ to $R_6 = H, R_3 = OSO_3H$ |
| 12. | L-glutamic acid, 3β-sulfonic acid | $Z = OH, R_1 = NH_2, R_2 = R_3 = R_5 = R_6 = H, R_4 = SO_3H$ |
| 13. | L-glutamic acid, 3β-sulfate | $Z = OH, R_1 = NH_2, R_2 = R_3 = R_5 = R_6 = H, R_4 = OSO_3H$ |

TABLE 2-continued

Structure 2

[Structure: Z-C(=O)-C(R5)(R6)-C(R3)(R4)-C(R1)(R2)-C(=O)-OH]

| | |
|---|---|
| 14. L-glutamic acid, 4α-sulfonic acid | Z = OH, $R_1$ = $NH_2$, $R_2$ = $R_3$ = $R_4$ = $R_6$ = H, $R_5$ = $SO_3H$ |
| 15. L-glutamic acid, 4α-sulfate | Z = OH, $R_1$ = $NH_2$, $R_2$ = $R_3$ = $R_4$ = $R_6$ = H, $R_5$ = $OSO_3H$ |
| 16. L-glutamic acid, 4β-sulfonic acid | Z = OH, $R_1$ = $NH_2$, $R_2$ to $R_5$ = H, $R_6$ = $SO_3H$ |
| 17. L-glutamic acid, 4β-sulfate | Z = OH, $R_1$ = $NH_2$, $R_2$ to $R_5$ = H, $R_6$ = $OSO_3H$ |
| 18. D-glutamic acid, N-sulfonic acid | Z = OH, $R_2$ = $NHSO_3H$, $R_1$, $R_3$ to $R_6$ = H |
| 19. 2β, 4-dicarboxy, butane-1-sulfonic acid | Z = OH, $R_2$ to $R_6$ = H, $R_1$ = $CH_2SO_3H$ |
| 20. 2β, 4-dicarboxy, butane-1-sulfate | Z = OH, $R_2$ to $R_6$ = H, $R_1$ = $CH_2OSO_3H$ |
| 21. D-glutamic acid, 2α-sulfonic acid | Z = OH, $R_2$ = $NH_2$, $R_3$ to $R_6$ H, $R_1$ = $SO_3H$ |
| 22. D-glutamic acid, 2α-sulfate | Z = OH, $R_2$ = $NH_2$, $R_3$ to $R_6$ H, $R_1$ = $OSO_3H$ |
| 23. D-glutamic acid, 3α-sulfonic acid | Z = OH, $R_2$ = $NH_2$, $R_1$, $R_4$ to $R_6$ H, $R_3$ = $SO_3H$ |
| 24. D-glutamic acid, 3α-sulfate | Z = OH, $R_2$ = $NH_2$, $R_1$, $R_4$ to $R_6$ H, $R_3$ = $OSO_3H$ |
| 25. D-glutamic acid, 3β-sulfonic acid | Z = OH, $R_2$ = $NH_2$, $R_1$ = $R_3$ = $R_5$ = $R_6$ = H, $R_4$ = $SO_3H$ |
| 26. D-glutamic acid, 3β-sulfate | Z = OH, $R_2$ = $NH_2$, $R_1$ = $R_3$ = $R_5$ = $R_6$ = H, $R_4$ = $OSO_3H$ |
| 27. D-glutamic acid, 4α-sulfonic acid | Z = OH, $R_2$ = $NH_2$, $R_1$ = $R_3$ = $R_4$ = $R_6$ = H, $R_5$ = $SO_3H$ |
| 28. D-glutamic acid, 4α-sulfate | Z = OH, $R_2$ = $NH_2$, $R_1$ = $R_3$ = $R_4$ = $R_6$ = H, $R_5$ = $OSO_3H$ |
| 29. D-glutamic acid, 4β-sulfonic acid | Z = OH, $R_2$ = $NH_2$, $R_1$ = $R_3$ = $R_4$ = $R_5$ = H, $R_6$ = $SO_3H$ |
| 30. D-glutamic acid, 4β-sulfate | Z = OH, $R_2$ = $NH_2$, $R_1$ = $R_3$ = $R_4$ = $R_5$ = H, $R_6$ = $OSO_3H$ |
| 31. L-glutamine, N-sulfonic acid | Z = $NH_2$, $R_1$ = $NHSO_3H$, $R_2$ to $R_6$ = H |
| 32. L-glutamine, 2β-sulfonic acid | Z = $R_1$ = $NH_2$, $R_3$ to $R_6$ = H, $R_2$ = $SO_3H$ |
| 33. L-glutamine, 2β-sulfate | Z = $R_1$ = $NH_2$, $R_3$ to $R_6$ = H, $R_2$ = $OSO_3H$ |
| 34. L-glutamine, 3α-sulfonic acid | Z = $R_1$ = $NH_2$, $R_2$ = H, $R_4$ to $R_6$ = H, $R_3$ = $SO_3H$ |
| 35. L-glutamine, 3α-sulfate | Z = $R_1$ = $NH_2$, $R_2$ = H, $R_4$ to $R_6$ = H, $R_3$ = $OSO_3H$ |
| 36. L-glutamine, 3β-sulfonic acid | Z = $R_1$ = $NH_2$, $R_2$ = $R_3$ = $R_5$ = $R_6$ = H, $R_4$ = $SO_3H$ |
| 37. L-glutamine, 3β-sulfate | Z = $R_1$ = $NH_2$, $R_2$ = $R_3$ = $R_5$ = $R_6$ = H, $R_4$ = $OSO_3H$ |
| 38. L-glutamine, 4α-sulfonic acid | Z = $R_1$ = $NH_2$, $R_2$ = $R_3$ = $R_4$ = $R_6$ = H, $R_5$ = $SO_3H$ |
| 39. L-glutamine, 4α-sulfate | Z = $R_1$ = $NH_2$, $R_2$ = $R_3$ = $R_4$ = $R_6$ = H, $R_5$ = $OSO_3H$ |
| 40. L-glutamine, 4β-sulfonic acid | Z = $R_1$ = $NH_2$, $R_2$ to $R_5$ = H, $R_6$ = $SO_3H$ |
| 41. L-glutamine, 4β-sulfate | Z = $R_1$ = $NH_2$, $R_2$ to $R_5$ = H, $R_6$ = $OSO_3H$ |
| 42. 2α-carboxy, 4-carboxamido, butane-1-sulfonic acid | Z = $NH_2$, $R_1$, $R_3$ to $R_6$ = H, $R_2$ = $CH_2SO_3H$ |
| 43. 2α-carboxy, 4-carboxamido, butane-1-sulfate | Z = $NH_2$, $R_1$, $R_3$ to $R_6$ = H, $R_2$ = $CH_2OSO_3H$ |
| 44. 1α-carboxy, 3-carboxamido, propane-1-sulfonic acid | Z = $NH_2$, $R_1$, $R_3$ to $R_6$ = H, $R_2$ = $SO_3H$ |
| 45. 1α-carboxy, 3-carboxamido, propane-1-sulfate | Z = $NH_2$, $R_1$, $R_3$ to $R_6$ = H, $R_2$ = $OSO_3H$ |
| 46. 1β-carboxy, 3-carboxamido, propane-1-sulfate | Z = $NH_2$, $R_2$ to $R_6$ = H, $R_1$ = $OSO_3H$ |
| 47. 1β-carboxy, 3-carboxamido, propane-1-sulfonic acid | Z = $NH_2$, $R_2$ to $R_6$ = H, $R_1$ = $SO_3H$ |
| 48. D-glutamine, N-sulfonic acid | Z = $NH_2$, $R_2$ = $NHSO_3H$; $R_1$ = H, $R_3$ to $R_6$ = H |
| 49. 2β-carboxy, 4-carboxamido, butane-1-sulfonic acid | Z = $NH_2$, $R_2$ to $R_6$ = H, $R_1$ = $CH_2SO_3H$ |
| 50. 2β-carboxy, 4-carboxamido, butane-1-sulfate | Z = $NH_2$, $R_2$ to $R_6$ = H, $R_1$ = $CH_2OSO_3H$ |
| 51. D-glutamine, 2α-sulfonic acid | Z = $NH_2$, $R_2$ = $NH_2$, $R_3$ to $R_6$ = H, $R_1$ = $SO_3H$ |
| 52. D-glutamine, 2α-sulfate | Z = $NH_2$, $R_2$ = $NH_2$, $R_3$ to $R_6$ = H, $R_1$ = $OSO_3H$ |
| 53. D-glutamine, 3α-sulfonic acid | Z = $NH_2$, $R_2$ = $NH_2$, $R_1$, $R_4$ to $R_6$ H, $R_3$ = $SO_3H$ |
| 54. D-glutamine, 3α-sulfate | Z = $R_2$ = $NH_2$, $R_1$, $R_4$ to $R_6$ H, $R_3$ = $OSO_3H$ |
| 55. D-glutamine, 3β-sulfonic acid | Z = $R_2$ = $NH_2$, $R_1$ = $R_3$ = $R_5$ = $R_6$ = H, $R_4$ = $SO_3H$ |
| 56. D-glutamine, 3β-sulfate | Z = $R_2$ = $NH_2$, $R_1$ = $R_3$ = $R_5$ = $R_6$ = H, $R_4$ = $OSO_3H$ |
| 57. D-glutamine, 4α-sulfonic acid | Z = $R_2$ = $NH_2$, $R_1$ = $R_3$ = $R_4$ = $R_6$ = H, $R_5$ = $SO_3H$ |
| 58. D-glutamine, 4α-sulfate | Z = $R_2$ = $NH_2$, $R_1$ = $R_3$ = $R_4$ = $R_6$ = H, $R_5$ = $OSO_3H$ |
| 59. D-glutamine, 4β-sulfonic acid | Z = $R_2$ = $NH_2$, $R_1$ = $R_3$ = $R_4$ = $R_5$ = H, $R_6$ = $SO_3H$ |
| 60. D-glutamine, 4β-sulfate | Z = $R_2$ = $NH_2$, $R_1$ = $R_3$ = $R_4$ = $R_5$ = H, $R_6$ = $OSO_3H$ |

TABLE 3 structure 3

[Structure: Z-C(=O)-C(R7)(R8)-C(R5)(R6)-C(R3)(R4)-C(R1)(R2)-C(=O)-OH]

| | |
|---|---|
| 1. L-homoglutamic acid, N-sulfonic acid | Z = OH, $R_1$ = $NHSO_3H$, $R_2$ to $R_8$ = H |
| 2. Pentane-2α, 5-dicarboxy-1-sulfonic acid | Z = OH, $R_1$, $R_3$ to $R_8$ = H, $R_2$ = $CH_2SO_3H$ |
| 3. Pentane-2α, 5-dicarboxy-1-sulfate | Z = OH, $R_1$, $R_3$ to $R_8$ = H, $R_2$ = $CH_2OSO_3H$ |
| 4. Butane-1α, 4-dicarboxy-1-sulfonic acid | Z = OH, $R_1$, $R_3$ to $R_8$ = H, $R_2$ = $SO_3H$ |
| 5. Butane-1α, 4-dicarboxy-1-sulfate | Z = OH, $R_1$, $R_3$ to $R_8$ = H, $R_2$ = $OSO_3H$ |
| 6. L-homoglutamic acid, 2β-sulfonic acid | Z = OH, $R_1$ = $NH_2$, $R_3$ to $R_8$ = H, $R_2$ = $SO_3H$ |
| 7. L-homoglutamic acid, 2β-sulfate | Z = OH, $R_1$ = $NH_2$, $R_3$ to $R_8$ = H, $R_2$ = $OSO_3H$ |
| 8. L-homoglutamic acid, 3α-sulfonic acid | Z = OH, $R_1$ = $NH_2$, $R_2$ = H, $R_4$ to $R_8$ H, $R_3$ = $SO_3H$ |
| 9. L-homoglutamic acid, 3α-sulfate | Z = OH, $R_1$ = $NH_2$, $R_2$ = H, $R_4$ to $R_8$ H, $R_3$ = $OSO_3H$ |
| 10. L-homoglutamic acid, 3β-sulfonic acid | Z = OH, $R_1$ = $NH_2$, $R_2$ = $R_3$ = H, $R_5$ to $R_8$ = H, $R_4$ = $SO_3H$ |

TABLE 3-continued

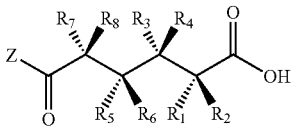

structure 3

11. L-homoglutamic acid, 3β-sulfate — Z = OH, $R_1$ = $NH_2$, $R_2$ = $R_3$ = H, $R_5$ to $R_8$ = H, $R_4$ = $OSO_3H$
12. L-homoglutamic acid, 4α-sulfonic acid — Z = OH, $R_1$ = $NH_2$, $R_2$ = $R_3$ = $R_4$ = H, $R_6$ to $R_8$ = H, $R_5$ = $SO_3H$
13. L-homoglutamic acid, 4α-sulfate — Z = OH, $R_1$ = $NH_2$, $R_2$ = $R_3$ = $R_4$ = H, $R_6$ to $R_8$ = H, $R_5$ = $OSO_3H$
14. L-homoglutamic acid, 4β-sulfonic acid — Z = OH, $R_1$ = $NH_2$, $R_2$ = $R_5$ = H, $R_7$ = $R_8$ = H, $R_6$ = $SO_3H$
15. L-homoglutamic acid, 4β-sulfate — Z = OH, $R_1$ = $NH_2$, $R_2$ = $R_5$ = H, $R_7$ = $R_8$ = H, $R_6$ = $OSO_3H$
16. L-homoglutamic acid, 5α-sulfonic acid — Z = OH, $R_1$ = $NH_2$, $R_2$ to $R_6$ = H, $R_8$ = H, $R_7$ = $SO_3H$
17. L-homoglutamic acid, 5α-sulfate — Z = OH, $R_1$ = $NH_2$, $R_2$ to $R_6$ = H, $R_8$ = H, $R_7$ = $OSO_3H$
18. L-homoglutamic acid, 5β-sulfonic acid — Z = OH, $R_1$ = $NH_2$, $R_2$ to $R_7$ = H, $R_8$ = $SO_3H$
19. L-homoglutamic acid, 5β-sulfate — Z = OH, $R_1$ = $NH_2$, $R_2$ to $R_7$ = H, $R_8$ = $OSO_3H$
20. D-homoglutamic acid, N-sulfonic acid — Z = OH, $R_2$ = $NHSO_3H$, $R_1$, $R_3$ to $R_8$ = H
21. Pentane-2β, 5-dicarboxy-1-sulfonic acid — Z = OH, $R_2$ to $R_8$ = H, $R_1$ = $CH_2SO_3H$
22. Pentane-2β, 5-dicarboxy-1-sulfate — Z = OH, $R_2$ to $R_8$ = H, $R_1$ = $CH_2OSO_3H$
23. Butane-1β, 4-dicarboxy-1-sulfonic acid — Z = OH, $R_2$ to $R_8$ = H, $R_1$ = $SO_3H$
24. Butane-1β, 4-dicarboxy-1-sulfate — Z = OH, $R_2$ to $R_8$ = H, $R_1$ = $OSO_3H$
25. D-homoglutamic acid, 2α-sulfonic acid — Z = OH, $R_2$ = $NH_2$, $R_3$ to $R_8$ = H, $R_1$ = $SO_3H$
26. D-homoglutamic acid, 2α-sulfate — Z = OH, $R_2$ = $NH_2$, $R_3$ to $R_8$ = H, $R_1$ = $OSO_3H$
27. D-homoglutamic acid, 3α-sulfonic acid — Z = OH, $R_2$ = $NH_2$, $R_1$, $R_4$ to $R_8$ = H, $R_3$ = $SO_3H$
28. D-homoglutamic acid, 3α-sulfate — Z = OH, $R_2$ = $NH_2$, $R_1$, $R_4$ to $R_8$ H, $R_3$ = $OSO_3H$
29. D-homoglutamic acid, 3β-sulfonic acid — Z = OH, $R_2$ = $NH_2$, $R_1$ = $R_3$ = H, $R_5$ to $R_8$ = H, $R_4$ = $SO_3H$
30. D-homoglutamic acid, 3β-sulfate — Z = OH, $R_2$ = $NH_2$, $R_1$ = $R_3$ = H, $R_5$ to $R_8$ = H, $R_4$ = $OSO_3H$
31. D-homoglutamic acid, 4α-sulfonic acid — Z = OH, $R_2$ = $NH_2$, $R_1$ = $R_3$ = $R_4$ = H, $R_6$ to $R_8$ = H, $R_5$ = $SO_3H$
32. D-homoglutamic acid, 4α-sulfate — Z = OH, $R_2$ = $NH_2$, $R_1$ = $R_3$ = $R_4$ = H, $R_6$ to $R_8$ = H, $R_5$ = $OSO_3H$
33. D-homoglutamic acid, 4β-sulfonic acid — Z = OH, $R_2$ = $NH_2$, $R_1$ = H, $R_3$ to $R_5$ = H, $R_7$ = $R_8$ = H, $R_6$ = $SO_3H$
34. D-homoglutamic acid, 4β-sulfate — Z = OH, $R_2$ = $NH_2$, $R_1$ = H, $R_3$ to $R_5$ = H, $R_7$ = $R_8$ = H, $R_6$ = $OSO_3H$
35. D-homoglutamic acid, 5α-sulfonic acid — Z = OH, $R_2$ = $NH_2$, $R_1$ = $R_8$ = H, $R_3$ to $R_6$ = H, $R_7$ = $SO_3H$
36. D-homoglutamic acid, 5α-sulfate — Z = OH, $R_2$ = $NH_2$, $R_1$ = $R_8$ = H, $R_3$ to $R_6$ = H, $R_7$ = $OSO_3H$
37. D-homoglutamic acid, 5β-sulfonic acid — Z = OH, $R_2$ = $NH_2$, $R_1$ = H, $R_3$ to $R_7$ = H, $R_8$ = $SO_3H$
38. D-homoglutamic acid, 5β-sulfate — Z = OH, $R_2$ = $NH_2$, $R_1$ = H, $R_3$ to $R_7$ = H, $R_8$ = $OSO_3H$
39. L-homoglutamine, N-sulfonic acid — Z = $NH_2$, $R_1$ = $NHSO_3H$, $R_2$ to $R_8$ = H
40. Pentane-2α-carboxy, 5-carboxamido-1-sulfonic acid — Z = $NH_2$, $R_1$ and $R_3$ to $R_8$ = H, $R_2$ = $CH_2SO_3H$
41. Pentane-2α-carboxy, 5-carboxamido-1-sulfate — Z = $NH_2$, $R_1$ and $R_3$ to $R_8$ = H, $R_2$ = $CH_2OSO_3H$
42. Butane-1α-carboxy, 4-carboxamido-1-sulfonic acid — Z = $NH_2$, $R_1$ and $R_3$ to $R_8$ = H, $R_2$ = $SO_3H$
43. Butane-1α-carboxy, 4-carboxamido-1-sulfate — Z = $NH_2$, $R_1$ and $R_3$ to $R_8$ = H, $R_2$ = $OSO_3H$
44. L-homoglutamine, 2β-sulfonic acid — Z = $R_1$ = $NH_2$, $R_3$ to $R_8$ = H, $R_2$ = $SO_3H$
45. L-homoglutamine, 2β-sulfate — Z = $R_1$ = $NH_2$, $R_3$ to $R_8$ = H, $R_2$ = $OSO_3H$
46. L-homoglutamine, 3α-sulfonic acid — Z = $R_1$ = $NH_2$, $R_2$ = H, $R_4$ to $R_8$ = H, $R_3$ = $SO_3H$
47. L-homoglutamine, 3α-sulfate — Z = $R_1$ = $NH_2$, $R_2$ = H, $R_4$ to $R_8$ = H, $R_3$ = $OSO_3H$
48. L-homoglutamine, 3β-sulfonic acid — Z = $R_1$ = $NH_2$, $R_2$ = $R_3$ = H, $R_5$ to $R_8$ = H, $R_4$ = $SO_3H$
49. L-homoglutamine, 3β-sulfate — Z = $R_1$ = $NH_2$, $R_2$ = $R_3$ = H, $R_5$ to $R_8$ = H, $R_4$ = $OSO_3H$
50. L-homoglutamine, 4α-sulfonic acid — Z = $R_1$ = $NH_2$, $R_2$ = $R_3$ = $R_4$ = H, $R_6$ to $R_8$ = H, $R_5$ = $SO_3H$
51. L-homoglutamine, 4α-sulfate — Z = $R_1$ = $NH_2$, $R_2$ = $R_3$ = $R_4$ = H, $R_6$ to $R_8$ = H, $R_5$ = $OSO_3H$
52. L-homoglutamine, 4β-sulfonic acid — Z = $R_1$ = $NH_2$, $R_2$ = $R_5$ = H, $R_7$ = $R_8$ = H, $R_6$ = $SO_3H$
53. L-homoglutamine, 4β-sulfate — Z = $R_1$ = $NH_2$, $R_2$ = $R_5$ = H, $R_7$ = $R_8$ = H, $R_6$ = $OSO_3H$
54. L-homoglutamine, 5α-sulfonic acid — Z = $R_1$ = $NH_2$, $R_2$ to $R_6$ = H, $R_8$ = H, $R_7$ = $SO_3H$
55. L-homoglutamine, 5α-sulfate — Z = $R_1$ = $NH_2$, $R_2$ to $R_6$ = H, $R_8$ = H, $R_7$ = $OSO_3H$
56. L-homoglutamine, 5β-sulfonic acid — Z = $R_1$ = $NH_2$, $R_2$ to $R_7$ = H, $R_8$ = $SO_3H$
57. L-homoglutamine, 5β-sulfate — Z = $R_1$ = $NH_2$, $R_2$ to $R_7$ = H, $R_8$ = $OSO_3H$
58. D-homoglutamine, N-sulfonic acid — Z = $NH_2$, $R_2$ = $NHSO_3H$, $R_1$ and $R_3$ to $R_8$ = H
59. Pentane-2β-carboxy, 5-carboxamido-1-sulfonic acid — Z = $NH_2$, $R_2$ to $R_8$ = H, $R_1$ = $CH_2SO_3H$
60. Pentane-2β-carboxy, 5-carboxamido-1-sulfate — Z = $NH_2$, $R_2$ to $R_8$ = H, $R_1$ = $CH_2OSO_3H$
61. Butane-1β-carboxy, 4-carboxamido-1-sulfonic acid — Z = $NH_2$, $R_2$ to $R_8$ = H, $R_1$ = $SO_3H$
62. Butane-1β-carboxy, 4-carboxamido-1-sulfate — Z = $NH_2$, $R_2$ to $R_8$ = H, $R_1$ = $OSO_3H$
63. D-homoglutamine, 2α-sulfonic acid — Z = $R_2$ = $NH_2$, $R_3$ to $R_8$ = H, $R_1$ = $SO_3H$
64. D-homoglutamine, 2α-sulfate — Z = $R_2$ = $NH_2$, $R_3$ to $R_8$ H, $R_1$ = $OSO_3H$
65. D-homoglutamine, 3α-sulfonic acid — Z = $R_2$ = $NH_2$, $R_1$, $R_4$ to $R_8$ H, $R_3$ = $SO_3H$
66. D-homoglutamine, 3α-sulfate — Z = $R_2$ = $NH_2$, $R_1$, $R_4$ to $R_8$ H, $R_3$ = $OSO_3H$
67. D-homoglutamine, 3β-sulfonic acid — Z = $R_2$ = $NH_2$, $R_1$ = $R_3$ = H, $R_5$ to $R_8$ = H, $R_4$ = $SO_3H$
68. D-homoglutamine, 3β-sulfate — Z = $R_2$ = $NH_2$, $R_1$ = $R_3$ = H, $R_5$ to $R_8$ = H, $R_4$ = $OSO_3H$
69. D-homoglutamine, 4α-sulfonic acid — Z = $R_2$ = $NH_2$, $R_1$ = $R_3$ = $R_4$ = H, $R_6$ to $R_8$ = H, $R_5$ = $SO_3H$
70. D-homoglutamine, 4α-sulfate — Z = $R_2$ = $NH_2$, $R_1$ = $R_3$ = $R_4$ = H, $R_6$ to $R_8$ = H, $R_5$ = $OSO_3H$
71. D-homoglutamine, 4β-sulfonic acid — Z = $R_2$ = $NH_2$, $R_1$ = H, $R_3$ to $R_5$ = H, $R_7$ = $R_8$ = H, $R_6$ = $SO_3H$
72. D-homoglutamine, 4β-sulfate — Z = $R_2$ = $NH_2$, $R_1$ = H, $R_3$ to $R_5$ = H, $R_7$ = $R_8$ = H, $R_6$ = $OSO_3H$
73. D-homoglutamine, 5α-sulfonic acid — Z = $R_2$ = $NH_2$, $R_1$ = $R_8$ = H, $R_3$ to $R_6$ = H, $R_7$ = $SO_3H$
74. D-homoglutamine, 5α-sulfate — Z = $R_2$ = $NH_2$, $R_1$ = $R_8$ = H, $R_3$ to $R_6$ = H, $R_7$ = $OSO_3H$
75. D-homoglutamine, 5β-sulfonic acid — Z = $R_2$ = $NH_2$, $R_1$ = H, $R_3$ to $R_7$ = H, $R_8$ = $SO_3H$
76. D-homoglutamine, 5β-sulfate — Z = $R_2$ = $NH_2$, $R_1$ = H, $R_3$ to $R_7$ = H, $R_8$ = $OSO_3H$

REFERENCE EXAMPLE

The following reference example and examples illustrate the present invention but do not limit the present invention.

The solvents in the parenthesis show the developing and eluting solvents and the ratios of the solvent used are by volume in the chromatographic separation or TLC.

The solvents in the parenthesis in NMR show the solvents used in measurement.

REFERENCE EXAMPLE AND EXAMPLE

The following reference example and examples illustrate the present invention but do not limit the present invention. The solvents in the parenthesis show the developing and eluting solvents and the ratios of the solvent used are by volume in the chromatographic separation or TLC. The solvents in the parenthesis in NMR show the solvents used in measurement.

Reference Example 1

L-glutamyl, N-sulfonic Acid from Glutamic Acid Mono Tertiary Butyl Ester

Glutamic acid monotertiary butyl ester (1 eq.) was added portion-wise to a solution of $SO_2Cl_2$ (2 eq.) in dry $CH_2Cl_2$ at 0° C. followed by $Et_3N$ (3 eq.). Resulting solution stirred for 8 hrs at r. t. when TLC showed complete consumption of starting material. Solvent was evaporated and the crude was dried in vacuum. 3 ml water was added to it and the slurry was stirred for 1 hr. To the slurry was added 45 ml $CH_2Cl_2$ followed by 3 eq of TFA at 0° C. The resulting solution was stirred at r. t. for 24 hrs. The solvent was evaporated and dried in vacuum. The pseudo molecular ion, $[M-H]^-$ at 226.0049 confirmed the structure of the product L-glutamyl, N-sulfonic acid (calculated for C5H8NO7S; 226.0026).

Reference Example 2

L-glutamyl, N-sulfonic Acid from Glutamic Acid Di Tertiary Butyl Ester

Glutamic acid ditertiary butyl ester (1 eq.) was added portion-wise to a solution of $SO_2Cl_2$ (2 eq.) in dry $CH_2Cl_2$ at 0° C. followed by $Et_3N$ (3 eq.). Resulting solution stirred for 8 hrs at r. t. when TLC showed complete consumption of starting material. Solvent was evaporated and the crude was dried in vacuum. 3 ml water was added to it and the slurry was stirred for 1 hr. To the slurry was added 45 ml $CH_2Cl_2$ followed by 3 eq of TFA at 0° C. The resulting solution was stirred at r. t. for 24 hrs. The solvent was evaporated and dried in vacuum. The pseudo molecular ion, $[M-H]^-$ at 226.0049 confirmed the structure of the product L-glutamyl, N-sulfonic acid (calculated for C5H8NO7S; 226.0026).

Reference Example 3

L-aspartyl, N-sulfonic Acid from L-aspartic Acid Di Tertiary Butyl Ester

L-aspartic acid di tertiary butyl ester (1 eq.) was added portion-wise to a solution of $SO_2Cl_2$ (2 eq.) in dry $CH_2Cl_2$ at 0° C. followed by $Et_3N$ (3 eq.). Resulting solution stirred for 8 hrs at r. t. when TLC showed complete consumption of starting material. Solvent was evaporated and the crude was dried in vacuum. 3 ml water was added to it and the slurry was stirred for 1 hr. To the slurry was added 45 ml $CH_2Cl_2$ followed by 3 eq of TFA at 0° C. The resulting solution was stirred at r. t. for 24 hrs. The solvent was evaporated and dried in vacuum. The pseudo molecular ion, $[M-H]^-$ at 211.9885 confirmed the structure of the product L-aspartyl, N-sulfonic acid (calculated for C4H6NO7S; 211.9870).

Reference Example 4

L-homoglutamyl, N-sulfonic Acid from L-homoglutamic Acid Di Tertiary Butyl Ester L-Homoglutamic acid di tertiary butyl ester (1 eq.) was added portion-wise to a solution of $SO_2Cl_2$ (2 eq.) in dry $CH_2Cl_2$ at 0° C. followed by $Et_3N$ (3 eq.). Resulting solution stirred for 8 hrs at r. t. when TLC showed complete consumption of starting material. Solvent was evaporated and the crude was dried in vacuum. 3 ml water was added to it and the slurry was stirred for 1 hr. To the slurry was added 45 ml $CH_2Cl_2$ followed by 3 eq of TFA at 0° C. The resulting solution was stirred at r. t. for 24 hrs. The solvent was evaporated and dried in vacuum. The pseudo molecular ion, $[M-H]^-$ at 240.0169 confirmed the structure of the product L-Homoglutamyl, N-sulfonic acid (calculated for C6H10NO7S; 240.0182).

Reference Example 5

The calcium salt of L-glutamyl-N-sulphonic acid was prepared by adding 1 M equivalent of $CaCl_2$ solution and incubated at temperature ranging from 30±5° C. The resulting complex was freeze-dried. The freeze-dried compound was reconstituted in sterilized distilled water and assessed in a dose-dependent manner for inhibition of osteoclast differentiation (Table A).

TABLE A

Effect of compound 1 (L-glutamyl-N-sulphonic acid, Ca salt) on osteoclast formation

| Culture conditions | Number of TRAP-positive multinuclear cells/well of 96 well plate (Mean ± SEM) | % inhibition |
| --- | --- | --- |
| M-CSF | 0 | — |
| M-CSF + RANKL | 138.00 ± 9.37 | — |
| M-CSF + RANKL + compound 1 (0.5 µg/ml) | 109.67 ± 9.79 | 21.01 |
| M-CSF + RANKL + compound 1 (1.5 µg/ml) | 52.17 ± 6.42 | 62.19 |
| M-CSF + RANKL + compound 1 (3.0 µg/ml) | 14.67 ± 1.98 | 89.36 |
| M-CSF + RANKL + compound 1 (5.0 µg/ml) | 2.83 ± 1.05 | 97.94 |

Culture of murine bone marrow cells in the presence of M-CSF and RANKL induces the formation of osteoclasts, which were detected as TRAP-positive cells. A dose dependent inhibition in the number of osteoclast cells generated as observed with increasing dose of compound 1. Values given are the mean±SD of five separate experiments

Reference Example 6

The calcium salt of L-glutamic acid was prepared by adding 1 M equivalent of $CaCl_2$ solution and incubated at temperature ranging from 30±5° C. The resulting complex was freeze-dried. The freeze-dried compound was reconstituted in sterilized distilled water and assessed in a dose-dependent manner for inhibition of osteoclast differentiation (Table B).

TABLE B

Effect of L-glutamic acid, calcium salt on osteoclast formation

| Culture conditions | Number of TRAP-positive multinuclear cells/well of 96 well plate (Mean ± SEM) | % inhibition |
|---|---|---|
| M-CSF | 0 | — |
| M-CSF + RANKL | 158.33 ± 12.00 | — |
| M-CSF + RANKL + compound 2 (0.5 µg/ml) | 167.17 ± 7.95 | 0 |
| M-CSF + RANKL + compound 2 (1.5 µg/ml) | 152.83 ± 10.47 | 3.47 |
| M-CSF + RANKL + compound 2 (3.0 µg/ml) | 130.50 ± 13.57 | 17.37 |
| M-CSF + RANKL + compound 2 (5.0 µg/ml) | 119.50 ± 10.00 | 24.52 |

For detail see legend to example 5

Reference Example 7

The L-glutamyl-N-sulphonic acid prepared as described in Examples 1 & 2 was reconstituted in sterilized distilled water and assessed in a dose-dependent manner for inhibition of osteoclast differentiation (Table D).

TABLE-D

Effect of L-glutamyl-N-sulphonic acid on osteoclast formation

| Culture conditions | Number of TRAP-positive multinuclear cells/well of 96 well plate (Mean ± SEM) | % inhibition |
|---|---|---|
| M-CSF | 0 | — |
| M-CSF + RANKL | 146.83 ± 11.89 | — |
| M-CSF + RANKL + compound 3 (0.5 µg/ml) | 154.67 ± 8.43 | 0 |
| M-CSF + RANKL + compound 3 (1.5 µg/ml) | 150.33 ± 8.82 | 0 |
| M-CSF + RANKL + compound 3 (3.0 µg/ml) | 112.67 ± 8.63 | 23.23 |
| M-CSF + RANKL + compound 3 (5.0 µg/ml) | 110.00 ± 6.72 | 25.08 |

For detail see legend to example 5

Reference Example 8

The L-glutamic acid was reconstituted in sterilized distilled water and assessed in a dose-dependent manner for inhibition of osteoclast differentiation (Table E).

TABLE E

Effect of L-glutamic acid on osteoclast formation

| Culture conditions | Number of TRAP-positive multinuclear cells/well of 96 well plate (Mean ± SEM) | % inhibition |
|---|---|---|
| M-CSF | 0 | — |
| M-CSF + RANKL | 156.00 ± 12.26 | 0 |
| M-CSF + RANKL + compound 4 (0.5 µg/ml) | 173.33 ± 6.50 | 0 |
| M-CSF + RANKL + compound 4 (1.5 µg/ml) | 155.00 ± 8.23 | 0.64 |
| M-CSF + RANKL + compound 4 (3.0 µg/ml) | 145.83 ± 14.71 | 7.05 |
| M-CSF + RANKL + compound 4 (5.0 µg/ml) | 112.67 ± 10.74 | 27.77 |

For detail see legend to example 5

Reference Example 9

The L-Aspartic acid, N-sulphonic acid as prepared in example 3 was mixed with 1 M equivalent of $CaCl_2$ solution and incubated at temperature ranging from 30±5° C. The resulting complex was freeze-dried. The freeze-dried compound was reconstituted in sterilized distilled water and assessed in a dose-dependent manner for inhibition of osteoclast differentiation (Table F).

TABLE F

Effect of L-Aspartic acid, N-sulphonic acid calcium salt on osteoclast formation

| Culture conditions | Number of TRAP-positive multinuclear cells/well of 96 well plate (Mean ± SEM) | % inhibition |
|---|---|---|
| M-CSF | 0 | — |
| M-CSF + RANKL | 158.33 ± 11.26 | 0 |
| M-CSF + RANKL + compound 4 (0.5 µg/ml) | 127.30 ± 5.50 | 19.70 |
| M-CSF + RANKL + compound 4 (1.5 µg/ml) | 86.23 ± 7.23 | 45.16 |
| M-CSF + RANKL + compound 4 (3.0 µg/ml) | 44.50 ± 4.80 | 71.90 |
| M-CSF + RANKL + compound 4 (5.0 µg/ml) | 26.67 ± 0.73 | 83.26 |

For detail see legend to example 5

Reference Example 10

L-homoglutamic acid, N-sulphonic acid as prepared in example 4 was mixed with 1 M equivalent of $CaCl_2$ solution and incubated at temperature ranging from 30±5° C. The resulting complex was freeze-dried. The freeze-dried compound was reconstituted in sterilized distilled water and assessed in a dose-dependent manner for inhibition of osteoclast differentiation (Table G).

TABLE G

Effect of L-homoglutamic acid, N-sulphonic acid, calcium salt on osteoclast formation

| Culture conditions | Number of TRAP-positive multinuclear cells/well of 96 well plate (Mean ± SEM) | % inhibition |
|---|---|---|
| M-CSF | 0 | — |
| M-CSF + RANKL | 146..83 ± 12.00 | — |
| M-CSF + RANKL + compound 2 (0.5 µg/ml) | 138.57 ± 7.95 | 5.55 |
| M-CSF + RANKL + compound 2 (1.5 µg/ml) | 106.23 ± 10.47 | 27.60 |
| M-CSF + RANKL + compound 2 (3.0 µg/ml) | 78.57 ± 13.57 | 46.40 |
| M-CSF + RANKL + compound 2 (5.0 µg/ml) | 46.22 ± 10.00 | 68.50 |

For detail see legend to example 5

Reference Example 11

A. In Vitro Osteoclastogenesis Assay

For in vitro osteoclastogenesis bone marrow cells were isolated from 5-to 8-wk-old Balb/c mice. Mice were sacrificed by cervical dislocation and femora and tibiae were aseptically removed and dissected free of adherent soft tissues. The bone ends were cut, and the marrow cavity was flushed out with medium MEM from one end of the bone using a sterile 21-gauge needle. The bone marrow suspension was carefully agitated with a plastic Pasteur pipette to obtain a single-cell suspension. The cells were washed twice and resuspended ($10^6$ cells/ml) in $\overline{\alpha}$MEM containing 10% FBS. Stromal cell-free, M-CSF-dependent, osteoclast precursor cells were prepared from these cells as previously described (Wani et al. 1999). Briefly, bone marrow cells were incubated for 24 h in $\overline{\alpha}$MEM containing 10% FBS in the presence of M-CSF (10 ng/ml) at a density of $3\times10^5$ cells/ml in a 75 cm$^2$ flask. After 24 h, nonadherent cells were harvested and layered on a Ficoll-Hypaque gradient. Cells at the gradient interface were collected, washed and resuspended ($5\times10^5$/ml) in $\overline{\alpha}$MEM containing 10% FBS. In this study, we called these stromal cell-free, M-CSF-dependent, nonadherent cells as osteoclast precursors. These osteoclast precursors were added to 96-well plates (100 µl/well) containing plastic coverslips. Each well received further 100 µl of medium containing M-CSF (30 ng/ml), RANKL (30 ng/ml) without or with various concentrations of purified compound. Cultures were fed every 2-3 days and after incubation for 6 days osteoclast formation was evaluated by tartrate-resistant acid phosphatase (TRAP) staining. The number of TRAP-positive multinucleated cells (MNCs) containing 3 or more nuclei was scored.

B. Characterization of Osteoclasts by TRAP Staining

Osteoclast formation was evaluated by quantification of TRAP-positive MNCs as described previously (Khapli et al. 2003). TRAP is preferentially expressed at high levels in osteoclast and is considered, especially in the mouse, to be an osteoclast marker. Cytochemical staining for TRAP is widely used for identifying the osteoclasts in vivo and in vitro. It is claimed to be specific for osteoclasts in bone. After incubation, cells on cover slips were washed in PBS, fixed in 10% formalin for 10 min and stained for acid phosphatase in the presence of 0.05 M sodium tartrate. The substrate used was napthol AS-BI phosphate. Only those cells that were strongly TRAP-positive (dark red) counted by light microscopy.

C. In Vitro Bone Resorption Assay

Osteoclast has the ability to excavate authentic resorption lacunae in vivo and in vitro. Bone resorption is the unique function of the osteoclast and is therefore the most useful means of distinguishing it from other cell types. M-CSF-dependent, non-adherent bone marrow cells were incubated for 10 days on bovine cortical bone slices in the presence of M-CSF, RANKL with or without various concentrations of compounds. Bone slices were examined for resorption pits by reflected light microscopy as previously described (Wani et al. 1999).

BRIEF DESCRIPTION OF THE FIGURES

The patent application file contains at least one drawing executed in color. Copies of this patent application publication with color drawings will be provided by the Office upon request and payment of the necessary fee.

Figure 1:
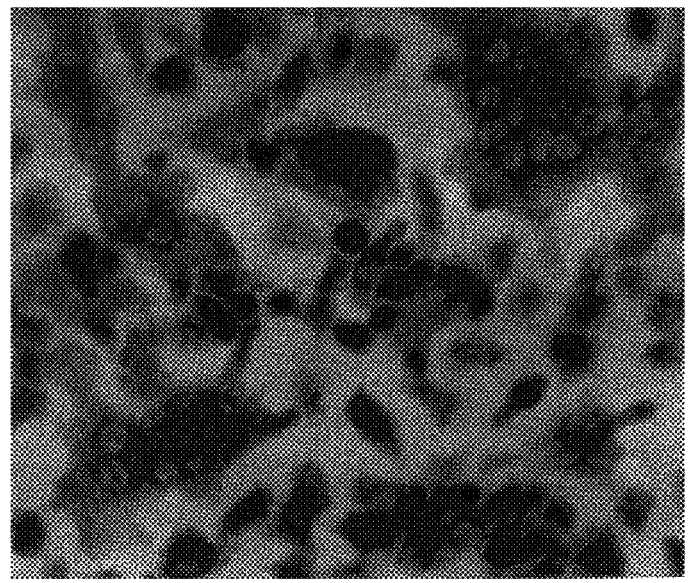
FIG. 1: Illustration of Plate 1: Effect of compound as given in example 3 on RANKL-induced osteoclast differentiation from haemopoietic precursors of monocytes/macrophage lineage. Mice osteoclast precursors were incubated in the presence of M-CSF and RANKL in the absence and presence of the compound. Photomicrographs showing TRAP-positive osteoclasts in the absence (Plate 1A) and presence (Plate 1B) of the compound. This compound significantly inhibited osteoclast formation.
Figure 1:
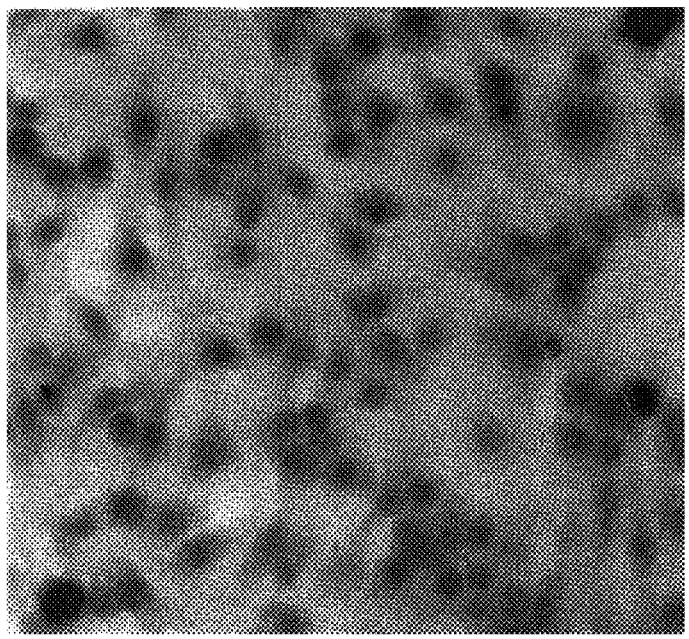
Figure 2:
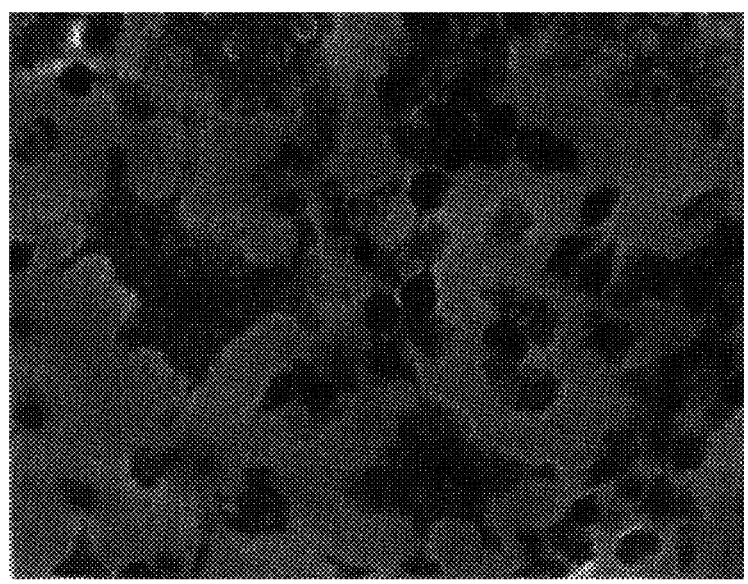
FIG. 2: Illustration of Plate 2: Effect of compound as described in example 4 on RANKL-induced osteoclast differentiation from haemopoietic precursors of monocytes/macrophage lineage. Photomicrographs showing TRAP-positive osteoclasts induced by M-CSF and RANKL in the absence (Plate 2A) and presence (Plate 2B) of the compound. This compound showed no inhibitory effect on osteoclast differentiation.
Figure 2:
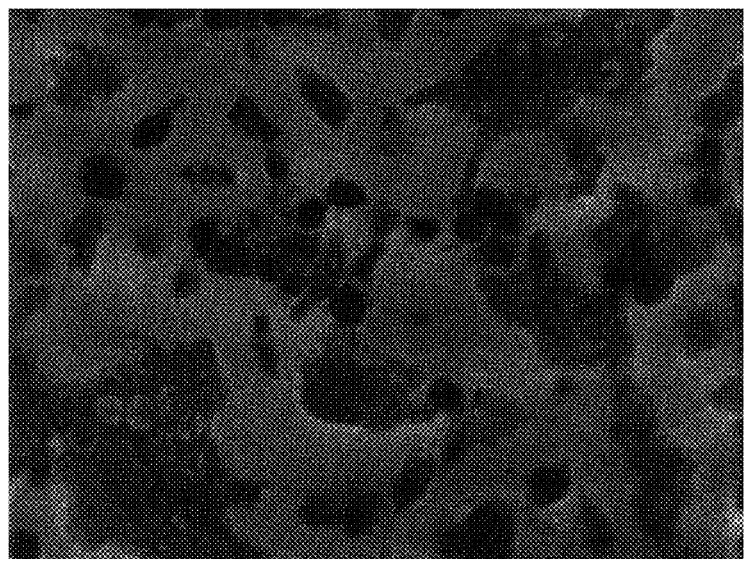

What is claimed is:

1. A method for inhibiting osteoclast formation in a subject in need thereof, comprising the step of administering a pharmaceutically effective amount of an isolated compound of the general formula ZOC—(CRR)$_m$—COOH, wherein: m=2, 3 or 4; Z is OH or NH$_2$; one R in the compound is from the group consisting of SO$_3$H, OSO$_3$H, CH$_2$—SO$_3$H, CH$_2$—OSO$_3$H, and NHSO$_3$H, and the remaining Rs are H or NH$_2$, optionally with an additive, excipient, diluent or carrier.

2. The method according to claim 1, for inhibiting formation of mononuclear TRAP-positive osteoclasts.

3. The method according to claim 1, for inhibiting formation of multinuclear TRAP-positive osteoclasts.

4. The method according to claim 1, wherein the pharmaceutically effective amount is 5 to 10 mg/kg of body weight.

5. The method according to claim 1, comprising administering the compound for between 5 and 30 days.

6. The method according to claim 1, comprising administering the compound for at least 30 days.

7. The method according to claim 1, comprising administering the compound for at least 60 days.

8. The method according to claim 1, comprising administering the compound for at least 90 days.

9. The method according to claim 1, wherein the compound has the structure shown below and the formula ZOC—CR$_3$R$_4$—CR$_1$R$_2$—COOH, wherein one of R$_1$ to R$_4$ is selected from the group consisting of SO$_3$H, OSO$_3$H, CH$_2$—SO$_3$H, CH$_2$—OSO$_3$H, and NHSO$_3$H, and the remaining are H or NH$_2$.

Structure 1

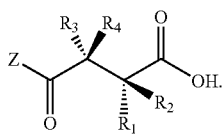

10. The method according to claim 1, wherein the compound has the structure shown below and the formula ZOC—CR$_5$R$_6$—CR$_3$R$_4$—CR$_1$R$_2$—COOH, wherein one of R$_1$ to R$_6$ is selected from the group consisting of SO$_3$H, OSO$_3$H, CH$_2$—SO$_3$H, CH$_2$—OSO$_3$H, and NHSO$_3$H, and the remaining are H or NH$_2$.

Structure 2

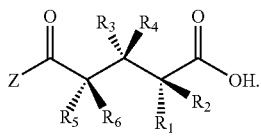

11. The method according to claim 1, wherein the compound has the structure shown below and the formula ZOC—CR$_7$R$_8$—CR$_5$R$_6$—CR$_3$R$_4$—CR$_1$R$_2$—COOH, wherein one of R$_1$ to R8 is selected from the group consisting of SO3H, OSO3H, CH2—SO3H, CH2—OSO3H, and NHSO$_3$H, and the remaining are H or NH$_2$.

structure 3

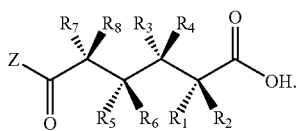

12. The method according to claim 9, wherein the compound is selected from the group consisting of:
 1. L-Aspartic acid, N-Sulfonic acid,
 2. L-Aspartic acid, 2β-sulfonic acid,
 3. L-Aspartic acid, 2β-sulfate,
 4. L-aspartic acid, 3α-sulfonic acid,
 5. L-aspartic acid, 3α-sulfate,
 6. L-aspartic acid, 3β-sulfonic acid,
 7. L-aspartic acid, 3f3-sulfate,
 8. 2α,3-dicarboxy, propane-1-sulfonic acid,
 9. 2α,3-dicarboxy, propane-1-sulfate,
 10. 1α,2-carboxy ethane sulfonic acid,
 11. 1α,2-carboxy ethane sulfate,
 12. D-aspartic acid, N-sulfonic acid,
 13. 2β,3-carboxy,propane-1-sulfonic acid,
 14. 2β,3-carboxy,propane-1-sulfate,
 15. 1β,2-carboxy ethane-1-sulfonic acid,
 16. 1β,2-carboxy ethane-1-sulfate,
 17. D-aspartic acid, 2α-sulfonic acid,
 18. D-aspartic acid, 2α-sulfonic acid,
 19. D-Aspartic acid, 3α-sulfonic acid,
 20. D-Aspartic acid, 3α-sulfate,
 21. D-Aspartic acid, 3β-sulfonic acid,
 22. D-aspartic acid, 3β-sulfate,
 23. L-asparagine,N-sulfonic acid,
 24. 2α-carboxy, 3-carboxamido, propane-1-sulfonic acid,
 25. 2α-carboxy, 3-carboxamido, propane-1-sulfate,
 26. 1α-carboxy, 2-carboxamido, ethane sulfonic acid,
 27. 1α-carboxy, 2-carboxamido, ethane sulfate,
 28. L-asparagine, 2β-sulfonic acid,
 29. L-asparagine, 2β-sulfate,
 30. L-asparagine, 3α-sulfonic acid,
 31. L-asparagine, 3α-sulfate,
 32. L-asparagine, 3β-sulfonic acid,
 33. L-asparagine, 3β-sulfate,
 34. D-asparagine, N-sulfonic acid,
 35. 2β-carboxy, 3-carboxamido, propane-1-sulfonic acid,
 36. 2β-carboxy, 3-carboxamido, propane-1-sulfate,
 37. 1β-carboxy, 2-carboxamido, ethane sulfonic acid,
 38. 1β-carboxy, 2-carboxamido, ethane sulfate,
 39. D-asparagine, 2α-sulfonic acid,
 40. D-asparagine, 2α-sulfate,
 41. D-asparagine, 3α-suifonic acid,
 42. D-asparagine, 3α-sulfate,
 43. D-asparagine, 3β-sulfonic acid,
 44. D-asparagine, 3β-sulfate.

13. The method according to claim 10, wherein the compound is selected from the group consisting of:
 (I) L-glutamic acid, N-sulfonic acid,
 (II) 2α,4-dicarboxy, butane-1-sulfonic acid,
 (III) 2α,4-dicarboxy, butane-1-sulfate,
 (IV) 1α,3-dicarboxy, propane sulfonic acid,
 (V) 1α,3-dicarboxy, propane sulfate,
 (VI) 1β,3-dicarboxy, propane sulfate,
 (VII) 1β,3-dicarboxy, propane sulfonic acid,
 (VIII) L-glutamic acid, 2β-sulfonic acid,
 (IX) L-glutamic acid, 2β-sulfate,
 (X) L-glutamic acid, 3α-sulfonic acid,
 (XI) L-glutamic acid, 3α-sulfate,
 (XII) L-glutamic acid, 3β-sulfonic acid,
 (XIII) L-glutamic acid, 3β-sulfate,
 (XIV) L-glutamic acid, 4α-sulfonic acid,
 (XV) L-glutamic acid, 4α-sulfate,
 (XVI) L-glutamic acid, 4β-sulfonic acid,
 (XVII) L-glutamic acid, 4β-sulfate,
 (XVIII) D-glutamic acid, N-sulfonic acid,
 (XIX) 2β,4-dicarboxy, butane-1-sulfonic acid,
 (XX) 2β,4-dicarboxy, butane-1-sulfate,
 (XXI) D-glutamic acid, 2α-sulfonic acid,
 (XXII) D-glutamic acid, 2α-sulfate,
 (XXIII) D-glutamic acid, 3α-sulfonic acid,
 (XXIV) D-glutamic acid, 3α-sulfate,
 (XXV) D-glutamic acid, 3β-sulfonic acid,
 (XXVI0 D-glutamic acid, 3β-sulfate,
 (XXVII) D-glutamic acid, 4α-sulfonic acid,
 (XXVIII) D-glutamic acid, 4α-sulfate,
 (XXIX) D-glutamic acid, 4β-sulfonic acid,
 (XXX) D-glutamic acid, 4β-sulfate,
 (XXXI) L-glutamine, N-sulfonic acid,
 (XXXII) L-glutamine, 2β-sulfonic acid,
 (XXXIII) L-glutamine, 2β-sulfate,
 (XXXIV) L-glutamine, 3α-sulfonic acid,
 (XXXV) L-glutamine, 3α-sulfate,
 (XXXVI) L-glutamine, 3β-sulfonic acid,
 (XXXVII) L-glutamine, 3β-sulfate,
 (XXXVIII) L-glutamine, 4α-sulfonic acid,
 (XXXIX) L-glutamine, 4α-sulfate,
 (XL) L-glutamine, 4β-sulfonic acid, (XLI) L-glutamine, 4β-sulfate,
(XLII) 2α-carboxy, 4-carboxamido, butane-1-sulfonic acid,
(XLIII) 2α-carboxy, 4-carboxamido, butane-1-sulfate,
(XLIV) 1α-carboxy, 3-carboxamido, propane-1-sulfonic acid,
(XLV) 1α-carboxy, 3-carboxamido, propane-1-sulfate,
(XLVI) 1β-carboxy, 3-carboxamido, propane-1-sulfate,
(XLVII) 1β-carboxy, 3-carboxamido, propane-1-sulfonic acid,
(XLVIII) D-glutamine, N-sulfonic acid,
(XLIX) 2β-carboxy, 4-carboxamido, butane-1-sulfonic acid,
(L) 2β-carboxy, 4-carboxamido, butane-1-sulfate,
(LI) D-glutamine, 2α-sulfonic acid,
(LII) D-glutamine, 2α-sulfate,
(LIII) D-glutamine, 3α-sulfonic acid,
(LIV) D-glutamine, 3α-sulfate,
(LV) D-glutamine, 3β-sulfonic acid,
(LVI) D-glutamine, 3β-sulfate,
(LVII) D-glutamine, 4α-sulfonic acid,
(LVIII) D-glutamine, 4α-sulfate,
(LIX) D-glutamine, 4β-sulfonic acid,
(LX) D-glutamine, 4β-sulfate.

14. The method according to claim 11, wherein the compound is selected from the group consisting of:
(I) L-homoglutamic acid, N-sulfonic acid,
(II) Pentane-2α,5-dicarboxy-1-sulfonic acid,
(III) Pentane-2α,5-dicarboxy-1-sulfate,
(IV) Butane-1α,4-dicarboxy-1-sulfonic acid,
(V) Butane-1α,4-dicarboxy-1-sulfate,
(VI) L-homoglutamic acid, 2β-sulfonic acid,
(VII) L-homoglutamic acid, 2β-sulfate,
(VIII) L-homoglutamic acid, 3α-sulfonic acid,
(IX) L-homoglutamic acid, 3α-sulfate,
(X) L-homoglutamic acid, 3β-sulfonic acid,
(XI) L-homoglutamic acid, 3β-sulfate,
(XII) L-homoglutamic acid, 4α-sulfonic acid,
(XIII) L-homoglutamic acid, 4α-sulfate,
(XIV) L-homoglutamic acid, 4β-sulfonic acid,
(XV) L-homoglutamic acid, 4β-sulfate,
(XVI) L-homoglutamic acid, 5α-sulfonic acid,
(XVII) L-homoglutamic acid, 5α-sulfate,
(XVIII) L-homoglutamic acid, 5β-sulfonic acid,
(XIX) L-homoglutamic acid, 5β-sulfate,
(XX) D-homoglutamic acid, N-sulfonic acid,
(XXI) Pentane-2β,5-dicarboxy-1-sulfonic acid,
(XXII) Pentane-2β,5-dicarboxy-1-sulfate,
(XXIII) Butane-1β,4-dicarboxy-1-sulfonic acid,
(XXIV) Butane-1β,4-dicarboxy-1-sulfate,
(XXV) D-homoglutamic acid, 2α-sulfonic acid,
(XXVI) D-homoglutamic acid, 2α-sulfate,
(XXVII) D-homoglutamic acid, 3α-sulfonic acid,
(XXVIII) D-homoglutamic acid, 3α-sulfate,
(XXIX) D-homoglutamic acid, 3β-sulfonic acid,
(XXX) D-homoglutamic acid, 3β-sulfate,
(XXXI) D-homoglutamic acid, 4α-sulfonic acid,
(XXXII) D-homoglutamic acid, 4α-sulfate,
(XXXIII) D-homoglutamic acid, 4β-sulfonic acid,
(XXXIV) D-homoglutamic acid, 4β-sulfate,
(XXXV) D-homoglutamic acid, 5α-sulfonic acid,
(XXXVI) D-homoglutamic acid, 5α-sulfate,
(XXXVII) D-homoglutamic acid, 5β-sulfonic acid,
(XXXVIII) D-homoglutamic acid, 5β-sulfate,
(XXXIX) L-homoglutamine, N-sulfonic acid,
(XL) Pentane-2α-carboxy, 5-carboxamido-1-sulfonic acid,
(XYLI) Pentane-2α-carboxy, 5-carboxamido-1-sulfate,
(XLII) Butane-1α-carboxy, 4-carboxamido-1-sulfonic acid,
(XLIII) Butane-1α-carboxy, 4-carboxamido-1-sulfate,
(XLIV) L-homoglutamine, 2β-sulfonic acid,
(XLV) L-homoglutamine, 2β-sulfate,
(XLVI) L-homoglutamine, 3α-sulfonic acid,
(XLVII) L-homoglutamine, 3α-sulfate,
(XLVIII) L-homoglutamine, 3β-sulfonic acid,
(XLIX) L-homoglutamine, 3β-sulfate,
(L) L-homoglutamine, 4α-sulfonic acid,
(LI) L-homoglutamine, 4α-sulfate,
(LII) L-homoglutamine, 4β-sulfonic acid,
(LIII) L-homoglutamine, 4β-sulfate,
(LIV) L-homoglutamine, 5α-sulfonic acid,
(LV) L-homoglutamine, 5α-sulfate,
(LVI) L-homoglutamine, 5β-sulfonic acid,
(LVII) L-homoglutamine, 5β-sulfate,
(LVIII) D-homoglutamine, N-sulfonic acid,
(LIX) Pentane-2β-carboxy, 5-carboxamido-1-sulfonic acid,
(LX) Pentane-2β-carboxy, 5-carboxamido-1-sulfate,
(LXI) Butane-1β-carboxy, 4-carboxamido-1-sulfonic acid,
(LXII) Butane-1β-carboxy, 4-carboxamido-1-sulfate,
(LXIII) D-homoglutamine, 2α-sulfonic acid,
(LXIV) D-homoglutamine, 2α-sulfate,
(LXV) D-homoglutamine, 3α-sulfonic acid,
(LXVI) D-homoglutamine, 3α-sulfate,
(LXVII) D-homoglutamine, 3β-sulfonic acid,
(LXVIII) D-homoglutamine, 3β-sulfate,
(LXIX) D-homoglutamine, 4α-sulfonic acid,
(LXX) D-homoglutamine, 4α-sulfate,
(LXXI) D-homoglutamine, 4β-sulfonic acid,
(LXXII) D-homoglutamine, 4β-sulfate,
(LXXIII) D-homoglutamine, 5α-sulfonic acid,
(LXXIV) D-homoglutamine, 5α-sulfate,
(LXXV) D-homoglutamine, 5β-sulfonic acid,
(LXXVI) D-homoglutamine, 5β-sulfate.

\* \* \* \* \*